(12) United States Patent
Cheng

(10) Patent No.: US 8,815,781 B2
(45) Date of Patent: Aug. 26, 2014

(54) METHOD FOR IMPROVING THE PROPERTIES OF A DRUG LEAD COMPOUND

(76) Inventor: Xueheng Cheng, Libertyville, IL (US)

(*) Notice: Subject to any disclaimer, the term of this patent is extended or adjusted under 35 U.S.C. 154(b) by 754 days.

(21) Appl. No.: 12/946,533

(22) Filed: Nov. 15, 2010

(65) Prior Publication Data

US 2011/0118124 A1    May 19, 2011

Related U.S. Application Data

(60) Provisional application No. 61/281,371, filed on Nov. 17, 2009.

(51) Int. Cl.
| | |
|---|---|
| *C40B 50/00* | (2006.01) |
| *C01B 9/08* | (2006.01) |
| *C07C 17/00* | (2006.01) |
| *G01N 33/94* | (2006.01) |
| *C07D 211/32* | (2006.01) |
| *C40B 40/04* | (2006.01) |
| *C07D 401/04* | (2006.01) |
| *C40B 30/04* | (2006.01) |
| *C40B 50/08* | (2006.01) |

(52) U.S. Cl.
CPC ............ *C40B 30/04* (2013.01); *G01N 33/94* (2013.01); *C01B 9/08* (2013.01); *C07C 17/00* (2013.01); *C07D 211/32* (2013.01); *C40B 50/08* (2013.01); *C40B 40/04* (2013.01); *C07D 401/04* (2013.01)

USPC ................. 506/23; 506/15; 506/27; 570/123

(58) Field of Classification Search
None
See application file for complete search history.

(56) References Cited

U.S. PATENT DOCUMENTS

2005/0064470 A1* 3/2005 Rana ................................ 435/6

OTHER PUBLICATIONS

Rentmeister et al. (Nat Chem Biol., 2009, 5(1): 26-28).*
Sanford et al. (Journal of Fluorine Chemistry, 2007, 128:90-104).*
Sun et al. (Amer. Soc. for Mass Spec., 2005, 16:271-279).*
Korfmacher et al. (Rapid Communications in Mass Spectrometry, 1999, 13:901-907).*
Blom et al. (J. Comb. Chem., 1999, 1:82-90).*

* cited by examiner

*Primary Examiner* — Christopher M Babic
*Assistant Examiner* — Jeremy C Flinders
(74) *Attorney, Agent, or Firm* — Justin Lampel

(57) ABSTRACT

The present patent application introduces methods for generating mixture compound libraries from a drug lead. The mixture compound libraries are then screened for the discovery of modified drug lead compounds which possess desired improved drug properties. The process utilizes a non-selective reaction to modify the drug lead compound structure. Compared to existing methods of modifying a drug lead compound, this new method can modify more structural positions of a drug lead compound. As a consequence, there will be greater probability of finding a product with improved drug properties.

29 Claims, 18 Drawing Sheets

METHOD FOR IMPROVING THE PROPERTIES OF A DRUG LEAD COMPOUND

CROSS REFERENCE TO RELATED APPLICATIONS

The present application claims priority benefit of U.S. Provisional Application 61/281,371, filed on Nov. 17, 2009, which is hereby incorporated by reference in its entirety.

FIELD OF THE INVENTION

The present method is directed to methods for improving the properties of a drug lead compound for drug development research.

BACKGROUND OF THE INVENTION

The modern drug discovery process often starts with identification of a compound which shows activities toward a biological target for a disease process; such a compound may be called a drug lead. The biological target may include, for example: a protein, a peptide, a nucleotide, a nucleic acid, a carbohydrate, an assembly of the above, a membrane, a cell, and/or a tissue. It is often necessary to improve a drug lead compound. Such improvement may be designed to, for example, make the drug lead have a high affinity or increased activity toward the biological target. The improvement may also be designed to improve the metabolic stability of the drug lead, improve the cell membrane permeability of the drug lead, etc. before the drug lead is generally selected as candidate for further development. In the process of improving the properties of the drug lead, a number of modified structures of the drug lead compound may first be designed. More specifically, the modified structures of the drug lead may be based on known mechanism of action of the drug lead and the structural information of the biological target. Alternatively, the modified structures of the drug lead may be based on chemical and/or biological intuitions, such as when the structure of the biological target or the mode of action of the drug lead is not precisely known. Next, the designed compounds may be synthesized, purified and tested individually for their properties. This process may be carried out several times before a modified drug lead having satisfying properties is discovered and selected for further development. Current methods of modifying a drug lead structure may be based on organic synthesis reactions with a primary goal of producing a desired single synthetic product having a high yield. (Nogrady, T. and Weaver, D. F., Medicinal chemistry: a molecular and biochemical approach, Oxford University Press, 2005; Thomas, G., Fundamentals of medicinal chemistry, Wiley, New York, 2003; Corey, E. J. and Cheng, X.-M., The Logic of Chemical Synthesis, Wiley, New York, 1989).

Often, the design of the structural modification is limited to known organic reactions at structural positions that may produce the desired single product in high yield. Accordingly, highly selective reactions are preferred for synthesizing the desired compound, one at a time. FIG. 1 of the present method illustrates such a process using a common drug, ibuprofen (RS)-2-(4-(2-methylpropyl)phenyl)propanoic acid) as an example of a drug lead. For a given drug lead compound, often there are only a few structural positions available for traditional modifications, as shown in FIG. 1. Methods are also available for making more than one structural modifications in the same reaction. A split synthesis technique may be implemented to make multiple products in a single reaction step. This technique has been used in drug discovery research.

(Nikolai F. Sepetov, et al. U.S. Pat. No. 6,799,120—Nonredundant split/pool synthesis of combinatorial libraries, US Patent Issued on Sep. 28, 2004; Lam, K. S., et al. "The 'one-bead-one-compound' combinatorial library method," Chem. Rev. 1997, 97, 411-448; Furka, A. and Bennett, W. D. "Combinatorial libraries by portioning and mixing," Comb. Chem. High Throughput Screening 1999, 2, 105-122). In the split synthesis process multiple parallel reactions are carried out, desired single product of each reaction are purified and are mixed together in the next reaction step to produce multiple products. This split synthesis method is illustrated in FIG. 2 again using ibuprofen as an example. Although the split synthesis technique can make multiple products in a single reaction step, the technique has the limitation that the modification is done only at structural positions where each of the multiple starting materials can produce the desired single product in high yield. Methods that can make modifications of a drug lead structure at more structural positions will produce products covering more structural space. That type of drug lead modification products will allow more fully examination of the effect of structural modification of a drug lead and will provide greater probability of finding modified structures with improved drug properties. Thus, there exists a need for methods that can more fully modify a drug lead structure for the discovery of compounds with improved drug properties. The present method satisfies this need and provides related advantages as well.

BRIEF SUMMARY OF THE INVENTION

The present patent application introduces methods for generating mixture compound libraries from a drug lead. The mixture compound libraries are then screened for the discovery of modified drug lead compounds which possess desired improved drug properties. The mixture compound library is defined as a compound mixture intentionally created for the purpose of testing multiple compounds concurrently for their drug properties where the mixture may contain two or more components of discrete organic compounds. The process utilizes a non-selective reaction to modify the drug lead compound structure. Compared to existing methods of modifying a drug lead compound, this new method can modify more structural positions of a drug lead compound. As a consequence, there will be greater probability of finding a product with improved drug properties.

A non-selective modification reaction produces a mixture product that introduces a substituent to most or all positions in the drug lead compound structure. This process is illustrated in FIG. 3, using ibuprofen as an example. Using a non-selective reaction to introduce a substituent to all C—H positions with one modification in each product, there will be a mixture of 7 possible products formed for ibuprofen without considering stereoisomers. Alternatively, non-selective modification may be done to a substructure compound of a drug lead to produce a mixture where the substituent is introduced to different positions of the drug lead substructure in different modification products. The modified drug lead substructure can be chemically linked with a complementary substructure, by a suitable organic reaction, to form the whole of the drug lead structure with non-selective modifications. This method of producing non-selective modification of a drug lead structure is illustrated in FIG. 4 using a known drug, gleevec (imatinib) as an example of drug lead. Known organic reactions that are non-selective include, but not limited to, reaction with fluorine gas (Gardiner, I. V., Fluorine Chemistry Research Advances, 2007, Nova Science Publishers, Inc. 2007; Pearson, B., Specialty Chemicals, Spring Innovations Ltd, 1991) and reaction with hydroxyl radical (Walling, C., Fenton's reagent revisited. Acc. Chem. Res., 1975, 8 (5), 125-131; Halliwell, B. and Gutteridge, J. M. C. Biologically relevant metal ion-dependent hydroxyl radical generation. An update. FEBS Lett., 1992, 307, 108-112; von Sonntag, C. The Chemical Basis of Radiation Biology, Taylor & Francis, London. 1987; Sharp, J. S.; et al. "Analysis of protein solvent accessible surfaces by photochemical oxidation and mass spectrometry," Anal. Chem. 2004, 76, 672-683). Oxidation reactions with cytochrom P450 enzymes can also lead to non-selective modification of a drug lead compound, especially if a mixture of different P450 enzymes is used. (Rentmeister, A., et al. Chemo-enzymatic fluorination of unactivated organic compounds, Nature Chemical Biology, 2009, 5 (1), 26-28)

Known methods, such as affinity selection LC-MS or NMR techniques, may be used to determine the affinity or activity of the mixture components toward a biological target. (Wanner, K. et al., Mass Spectrometry in Medicinal Chemistry: Applications in Drug Discovery, Volume 36, Wiley 2007; Comess, K. M. and Schurdak, M. E., Affinity-based screening techniques for enhancing lead discovery, Current Opinion in Drug Discovery & Development 2004, 7 (4), 411-416; Klages, J. et al. NMR-based screening: a powerful tool in fragment-based drug discovery, Analyst, 2007, 132, 692-705; Lepre, C. A., et al. Theory and applications of NMR-based screening in pharmaceutical research. Chemical Reviews, 2004, 104 (8), 3641-3675) Known methods may also be used to determine metabolic stability of compounds, such as commonly used human microsomal stability testing with LC-MS analysis. (Halladay, J. S. et al. Metabolic Stability Screen for Drug Discovery Using Cassette Analysis and Column Switching, Drug Metabolism Letters, 2007, 1, 67-72) Known purification methods such as HPLC with UV and mass spectrometry detection can be used to purify those mixture components which demonstrate improved properties. (Blom K. F., et al. Preparative LC-MS purification: improved compound-specific method optimization, J Comb Chem. 2004, 6 (6), 874-83) The purified components may be tested individually to confirm the improved drug properties relative to the original drug lead compound. The new methods of this application provide a more extensive modification than traditional methods of the structural positions of the drug lead compound. Further, the present methods provide for improved screening for the discovery of new compounds with better drug properties. It is also possible to utilize both this new method of non-selective modification and traditional methods of selective modification of a drug lead to achieve an exhaustive search for new structures with improved drug properties.

BRIEF DESCRIPTION OF THE DRAWINGS

Other features and advantages of the present method will be apparent from the following description of the preferred embodiments thereof and from the claims, taken in conjunction with the accompanying drawings, in which:

DETAILED DESCRIPTION OF THE METHOD

The present patent application introduces methods for generating mixture compound libraries from a drug lead. The mixture compound libraries are then screened for the discovery of modified drug lead compounds which possess desired improved drug properties. The mixture compound library is defined as a compound mixture intentionally created for the purpose of testing multiple compounds concurrently for their drug properties where the mixture may contain two or more components of discrete organic compounds. The process utilizes a non-selective reaction to modify the drug lead compound structure. Compared to existing methods of modifying a drug lead compound, this new method can modify more structural positions of a drug lead compound. As a consequence, there will be greater probability of finding a product with improved drug properties.

Figure 1:
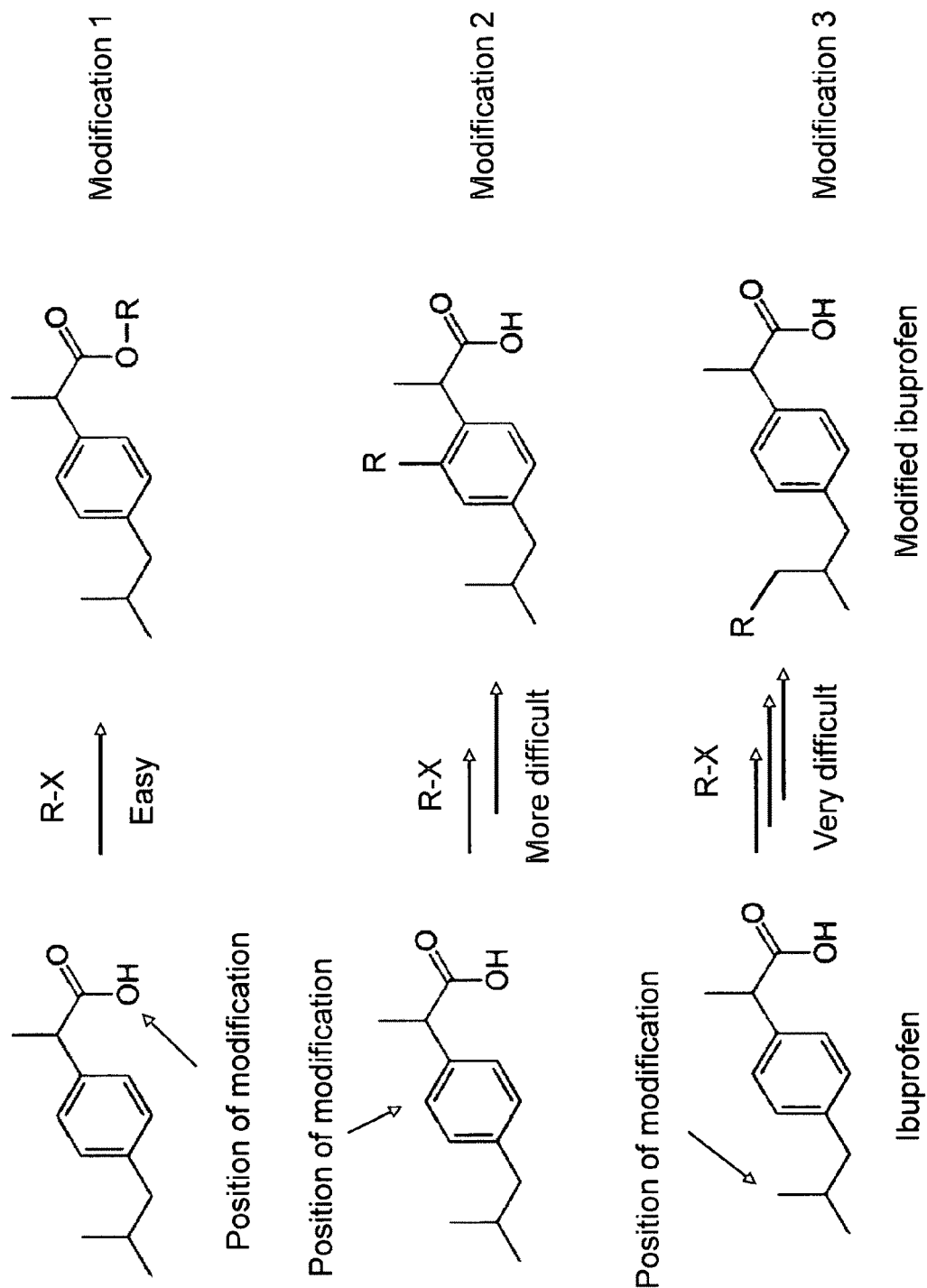
FIG. 1 illustrates traditional methods of structural modification using ibuprofen as an example.

FIG. 1 illustrates traditional methods of structural modification using ibuprofen as an example: modification is done selectively, one structural position at a time, made using selective organic synthesis reactions. R—X is a reagent for structural modification and R is the functional group introduced in the structural modification. Modification 1 can be done routinely with high selectivity; modification 2 is more difficult to achieve selectively, may require multiple-step reactions or purification out of mixture products; modification 3 is very difficult to achieve, requiring multiple step reactions or purification out of mixture products.

Figure 2:
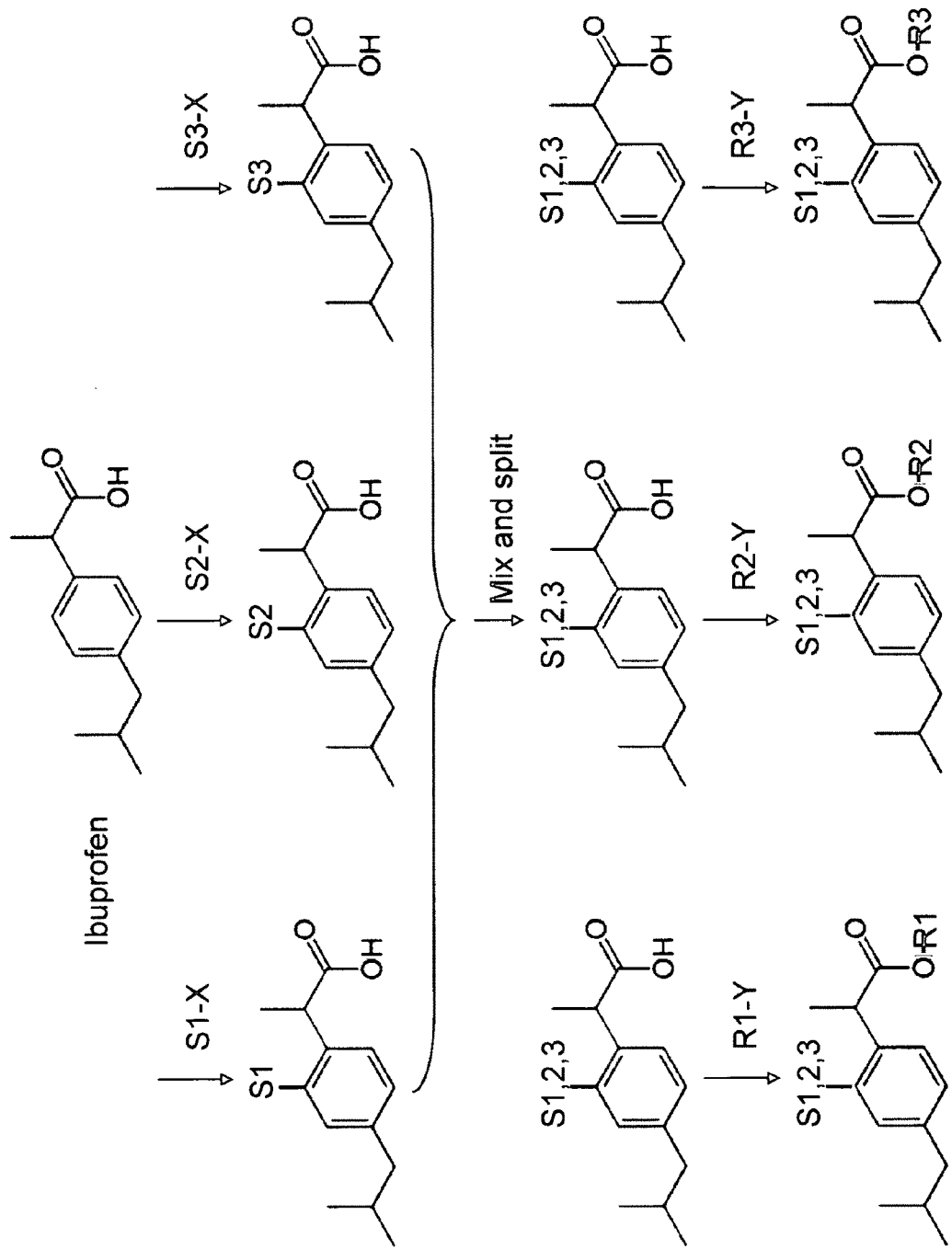
FIG. 2 illustrates split synthesis method for structural modification using ibuprofen as an example.

FIG. 2 illustrates split synthesis method for structural modification using ibuprofen as an example: modification is done selectively, one position at a time, made using selective organic synthesis reactions. Multiple products are produced by mixing and splitting. S1-X, S2-X, S3-X, R1-Y, R2-Y, R3-Y are reagents for structural modification and S1, S2, S3, R1, R2, R3 are the functional groups introduced in the modification.

Figure 3:
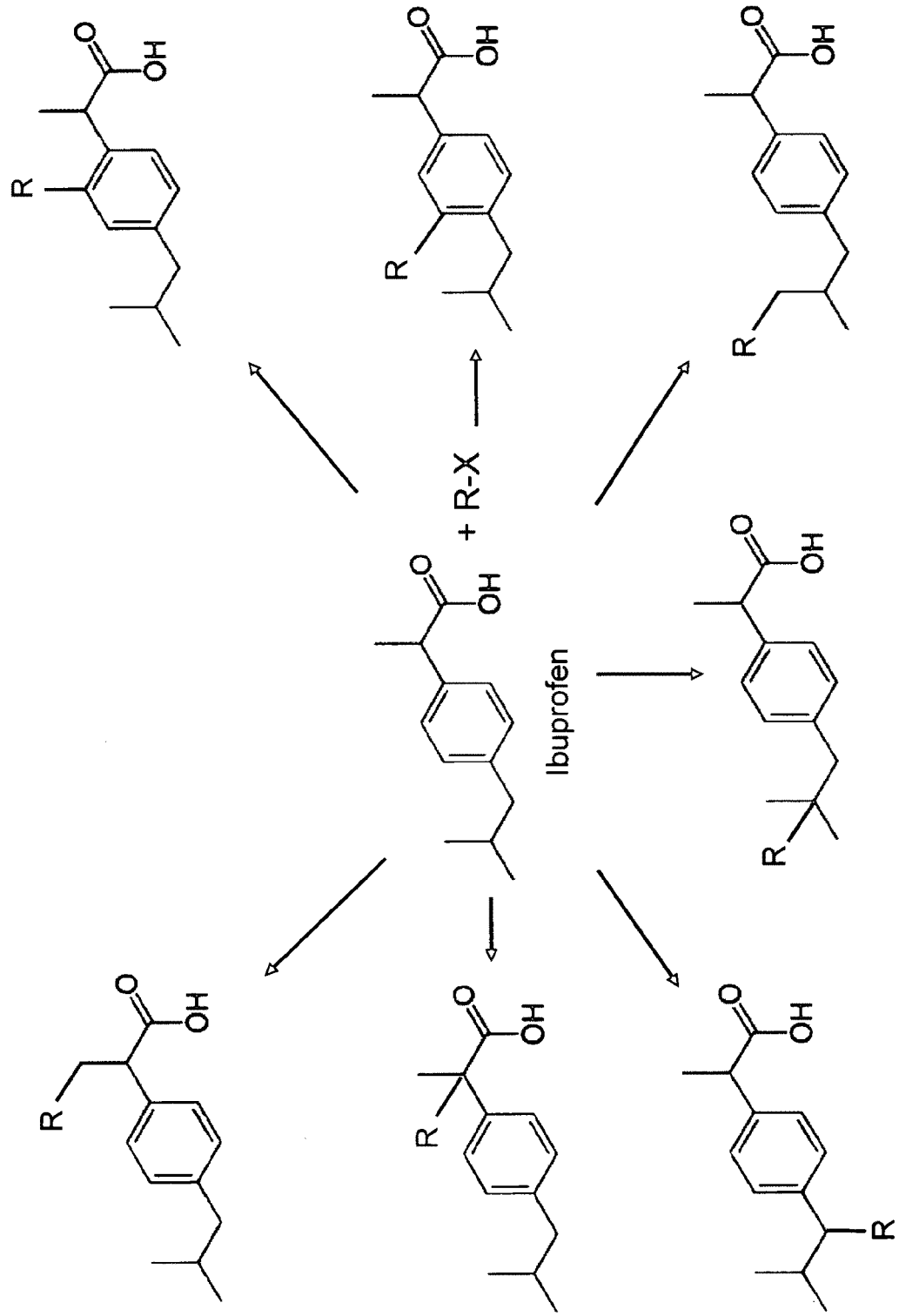
FIG. 3 illustrates the new method of structural modification introduced in this method using ibuprofen as an example.

FIG. 3 illustrates the new method of structural modification introduced in this application using ibuprofen as an example: modification is done non-selectively, all structural positions containing a C—H bond are modified, one modification in each product will result in 7 possible products. R—X is a reagent for structural modification and R is the functional group introduced in the structural modification.

Figure 4:
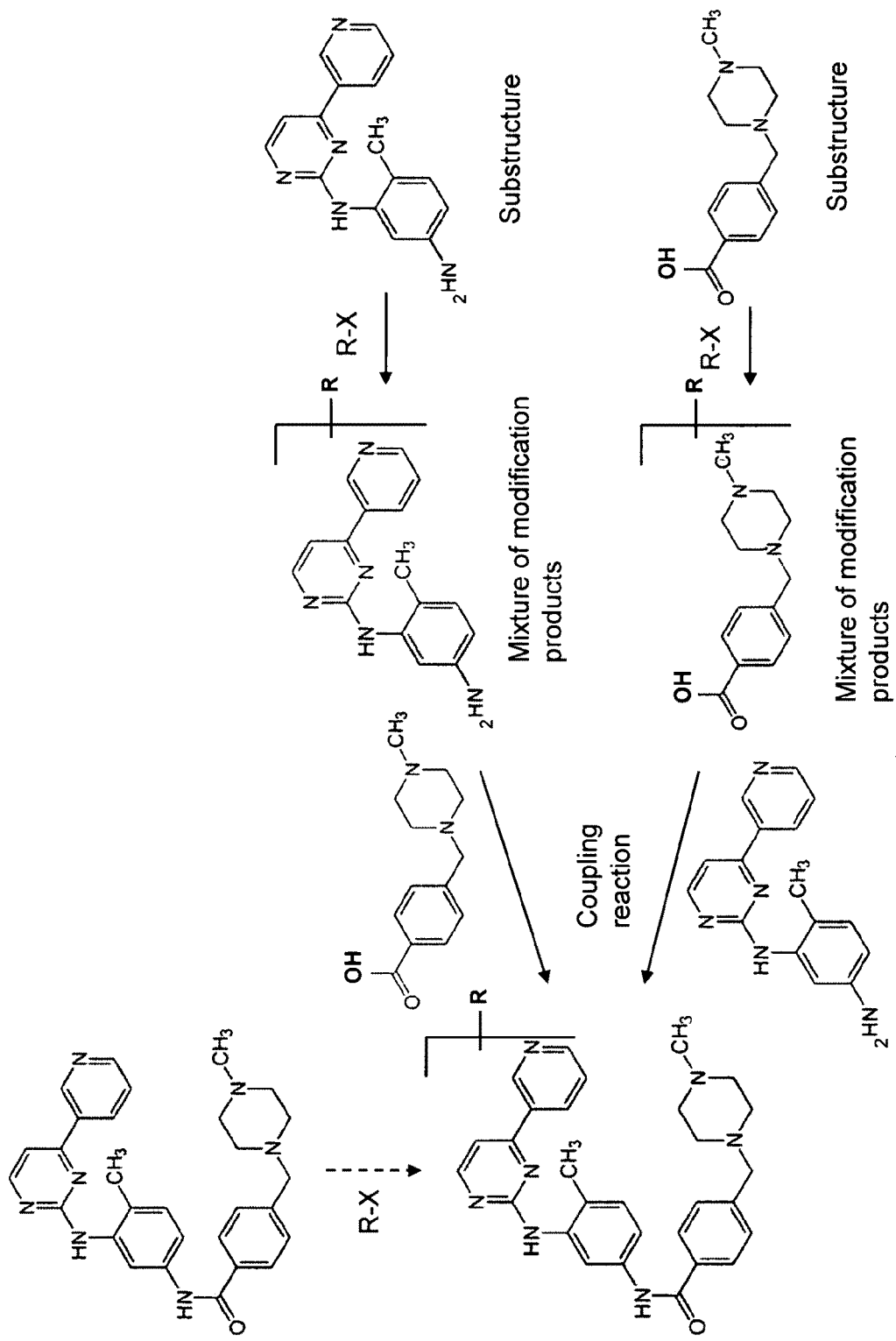
FIG. 4 illustrates non-selective modification of a drug lead compound by non-selective modification of the substructures of the drug lead and linking the substructures together.

FIG. 4 illustrates non-selective modification of a drug lead compound by non-selective modification of the substructures of the drug lead and linking the substructures together. A known drug gleevec is used as an example. R—X is a reagent for structural modification and R is the functional group introduced in the structural modification.

Figure 5A:
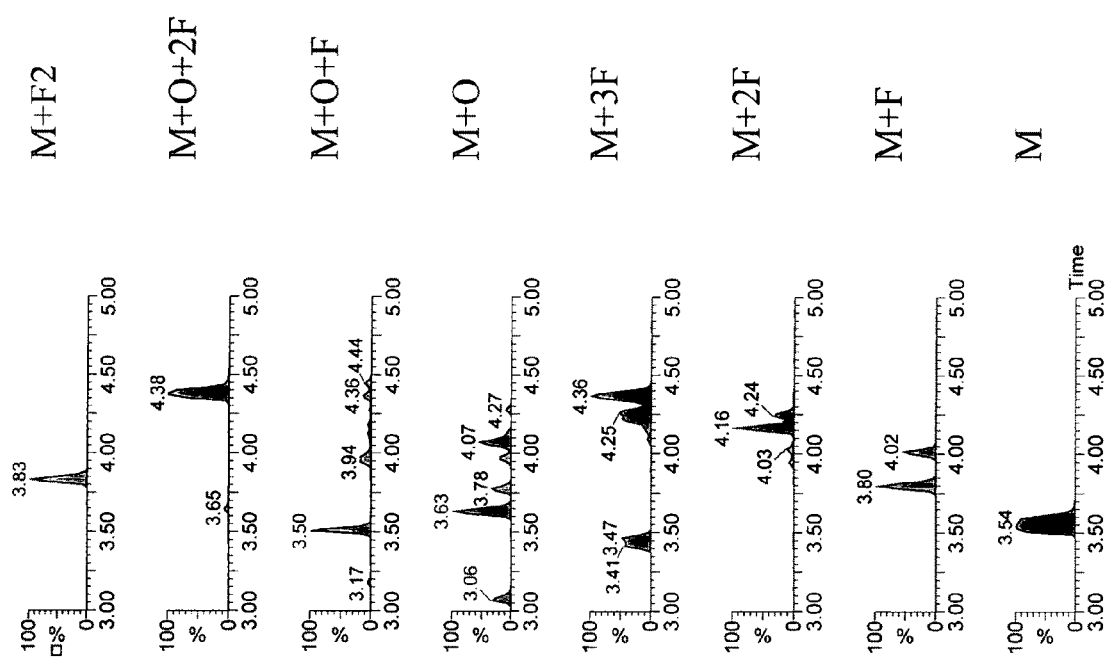
FIG. 5a shows LC-MS single ion chromatogram of selected products of reaction of donepezil with fluorine gas at −78° C. for 30 min.

FIG. 5a shows LC-MS single ion chromatogram of selected products of reaction of donepezil with fluorine gas at −78° C. for 30 min.

Figure 5B:
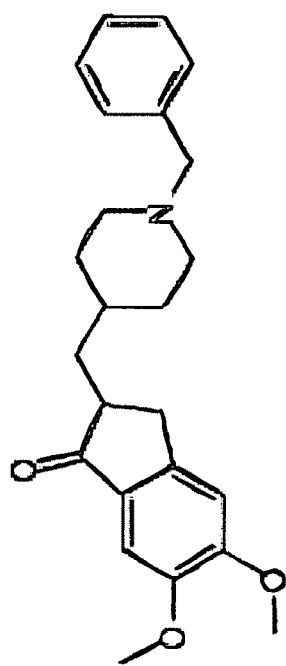
FIG. 5b shows structure of donepezil.

FIG. 5b shows structure of donepezil.

Figure 5C:
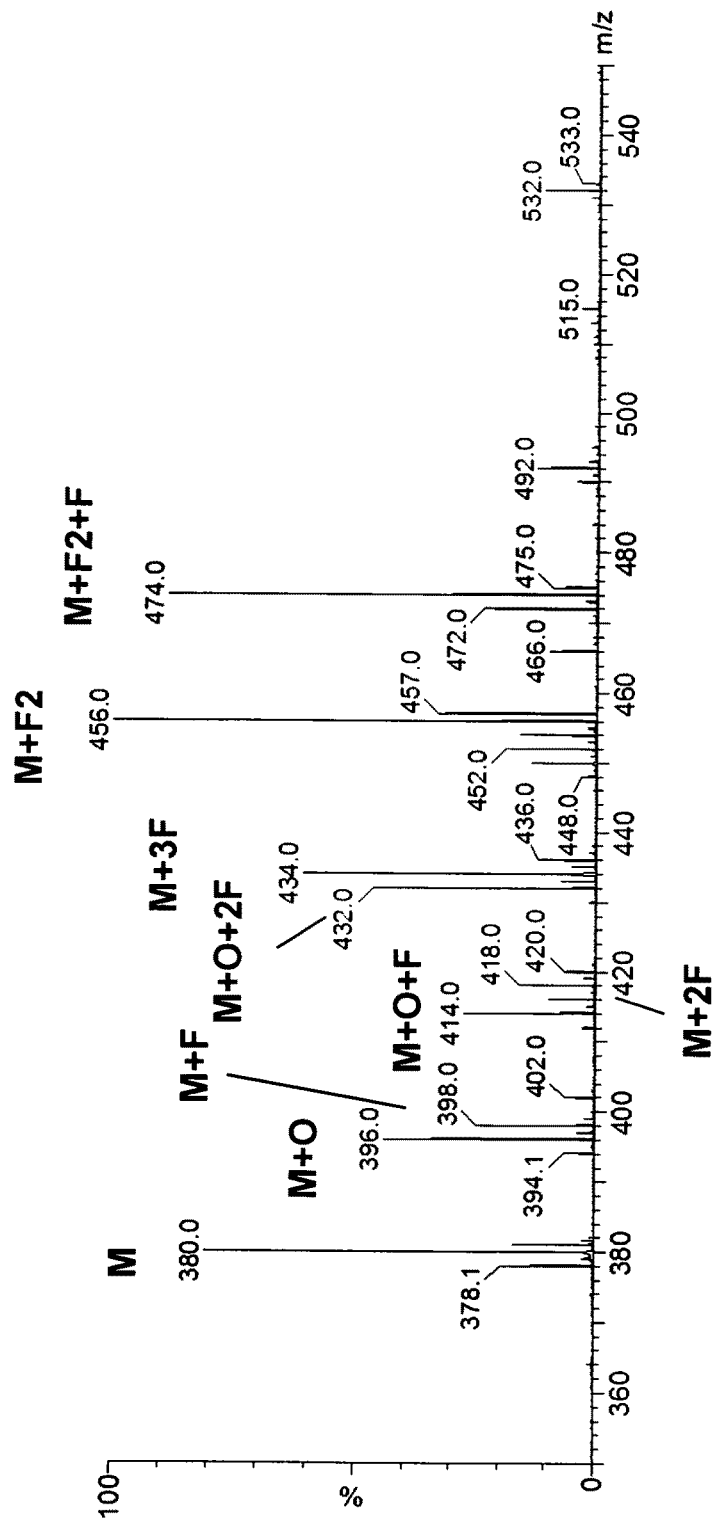
FIG. 5c shows mass spectrum of products of reaction of donepezil with fluorine gas at −78° C. for 30 min.

FIG. 5c shows mass spectrum of products of reaction of donepezil with fluorine gas at −78° C. for 30 min.

Figure 6:
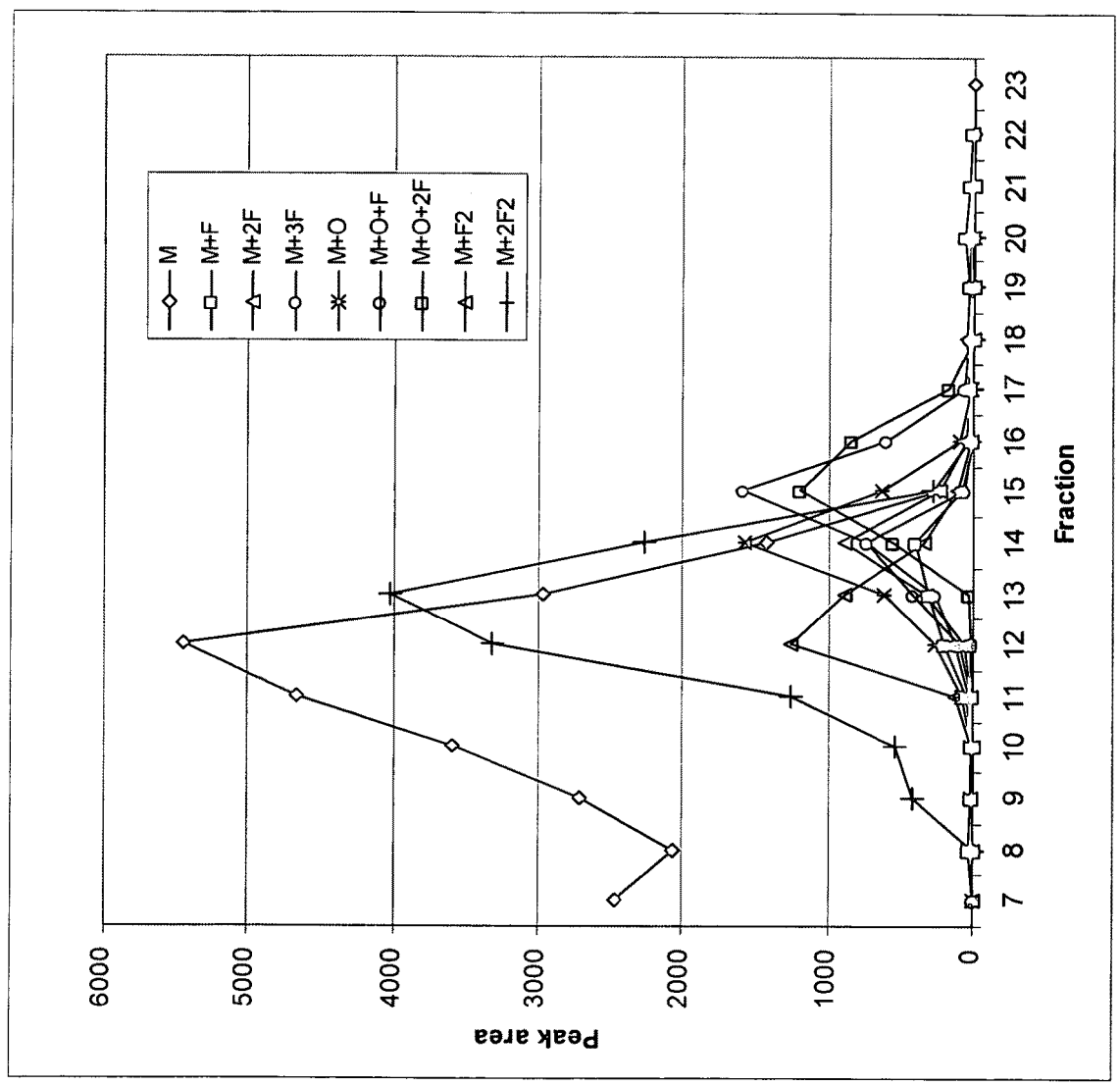
FIG. 6 shows separation of the products of non-selective fluorination reaction of donepezil using LC-MS. Donepezil fluorination mixture library 1 was created by combing the fraction No 14-No 16 from this separation.

FIG. 6 shows separation of the products of non-selective fluorination reaction of donepezil using LC-MS. Donepezil fluorination mixture library 1 was created by combing the fraction No 14-No 16 from this separation.

Figure 7:
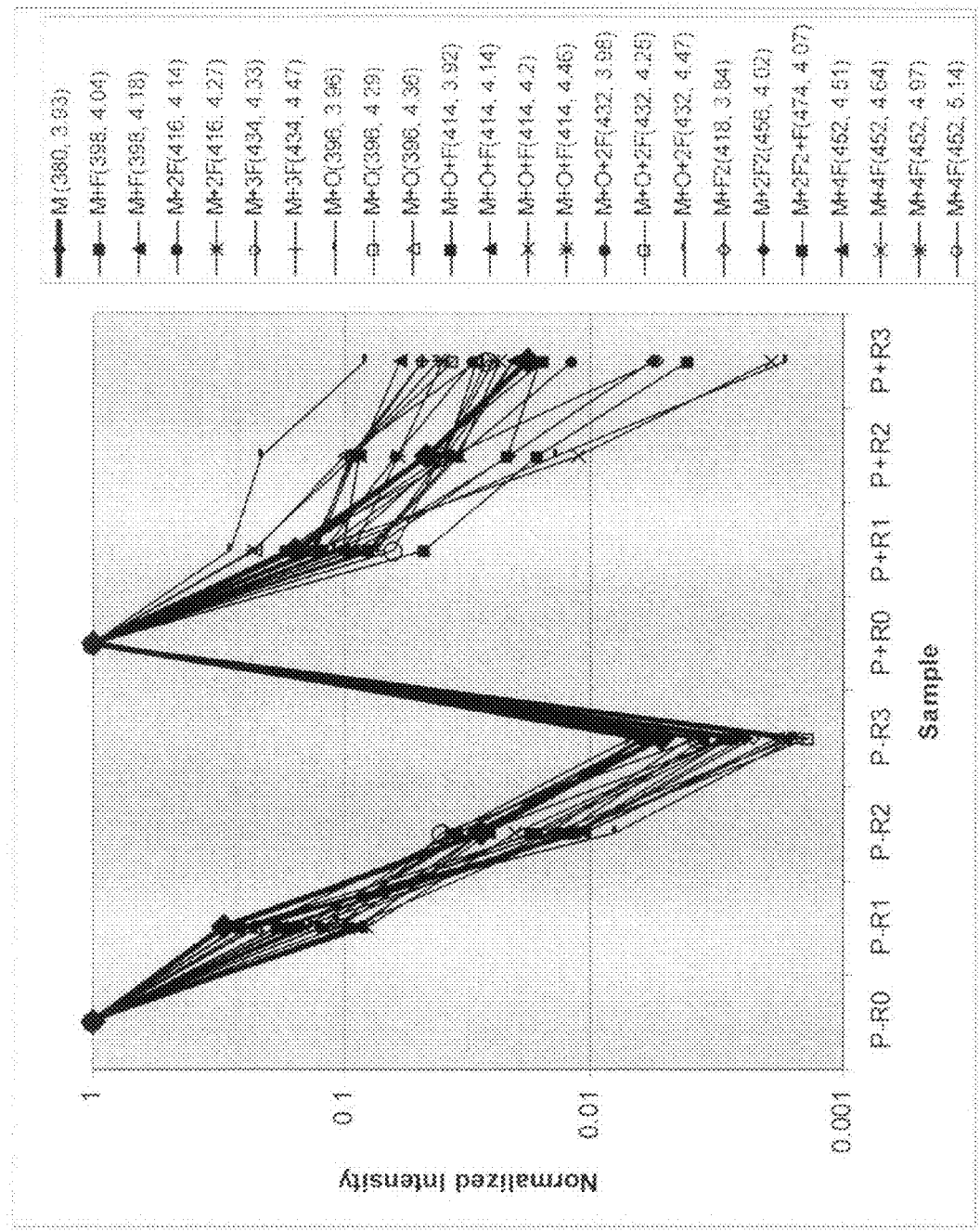
FIG. 7 shows results of affinity testing of donepezil fluorination mixture library 1 against AChE enzyme.

FIG. 7 shows results of affinity testing of donepezil fluorination mixture library 1 against AChE enzyme.

Figure 8:
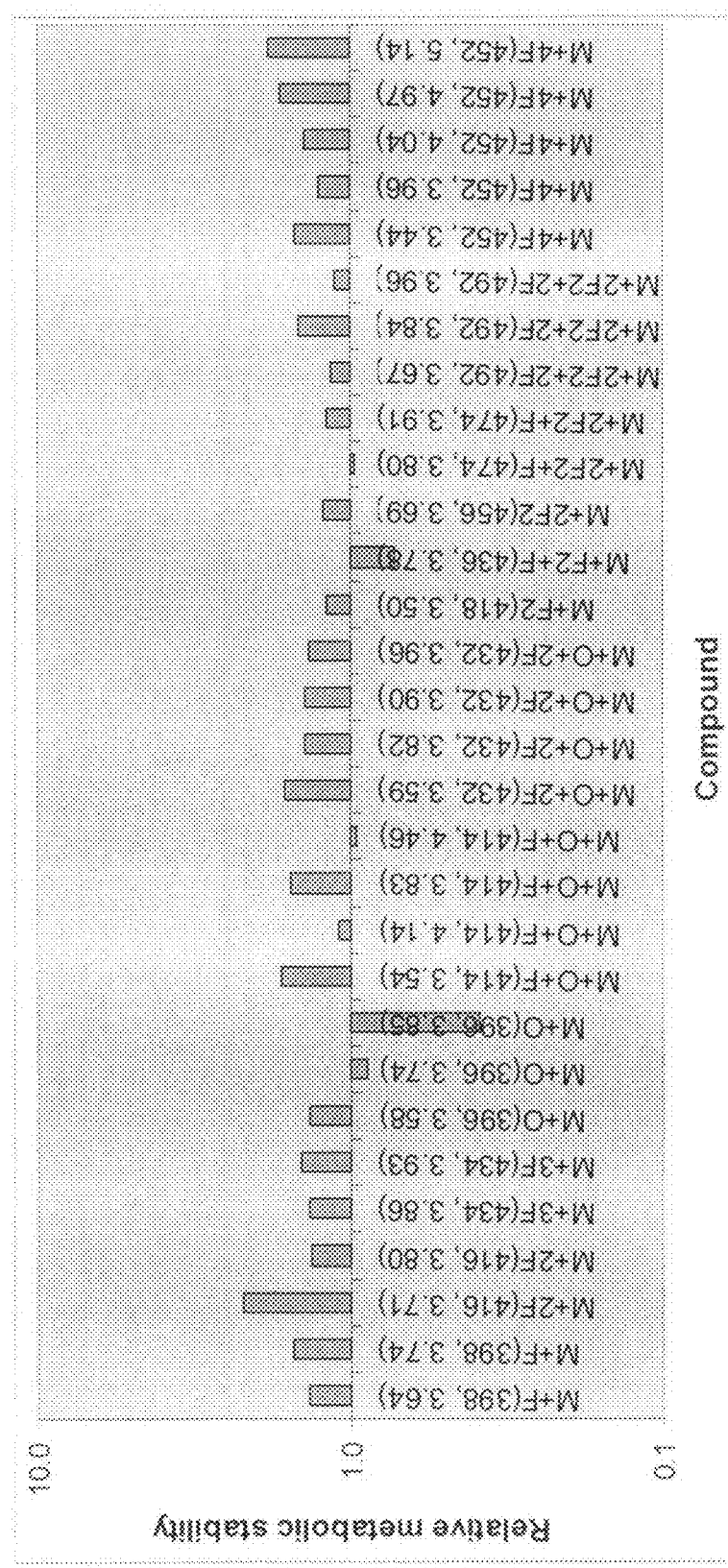
FIG. 8 shows results of human liver microsome stability testing of donepezil fluorination mixture library 1.

FIG. 8 shows results of human liver microsome stability testing of donepezil fluorination mixture library 1.

Figure 9A:
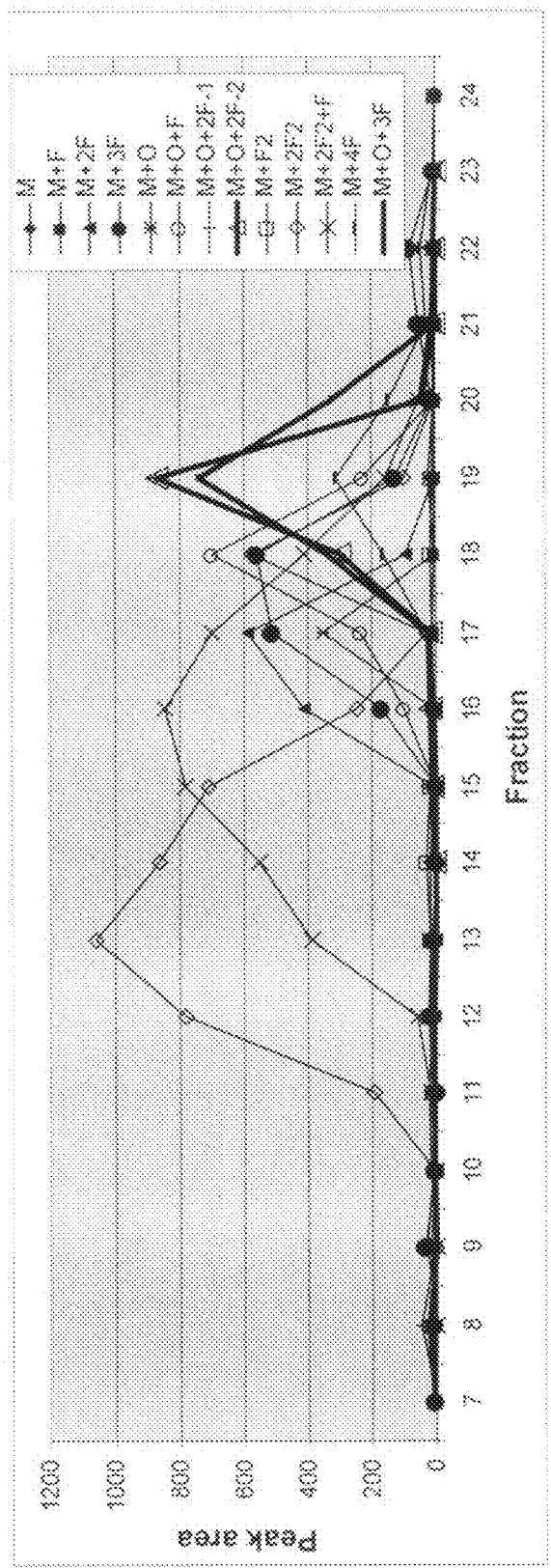
FIGS. 9a and 9b show LC-MS analysis of fractions from separation of donepezil fluorination mixture library 1 by HPLC.

FIG. 9a shows LC-MS analysis of fractions from separation of donepezil fluorination mixture library 1 by HPLC.

Figure 9B:
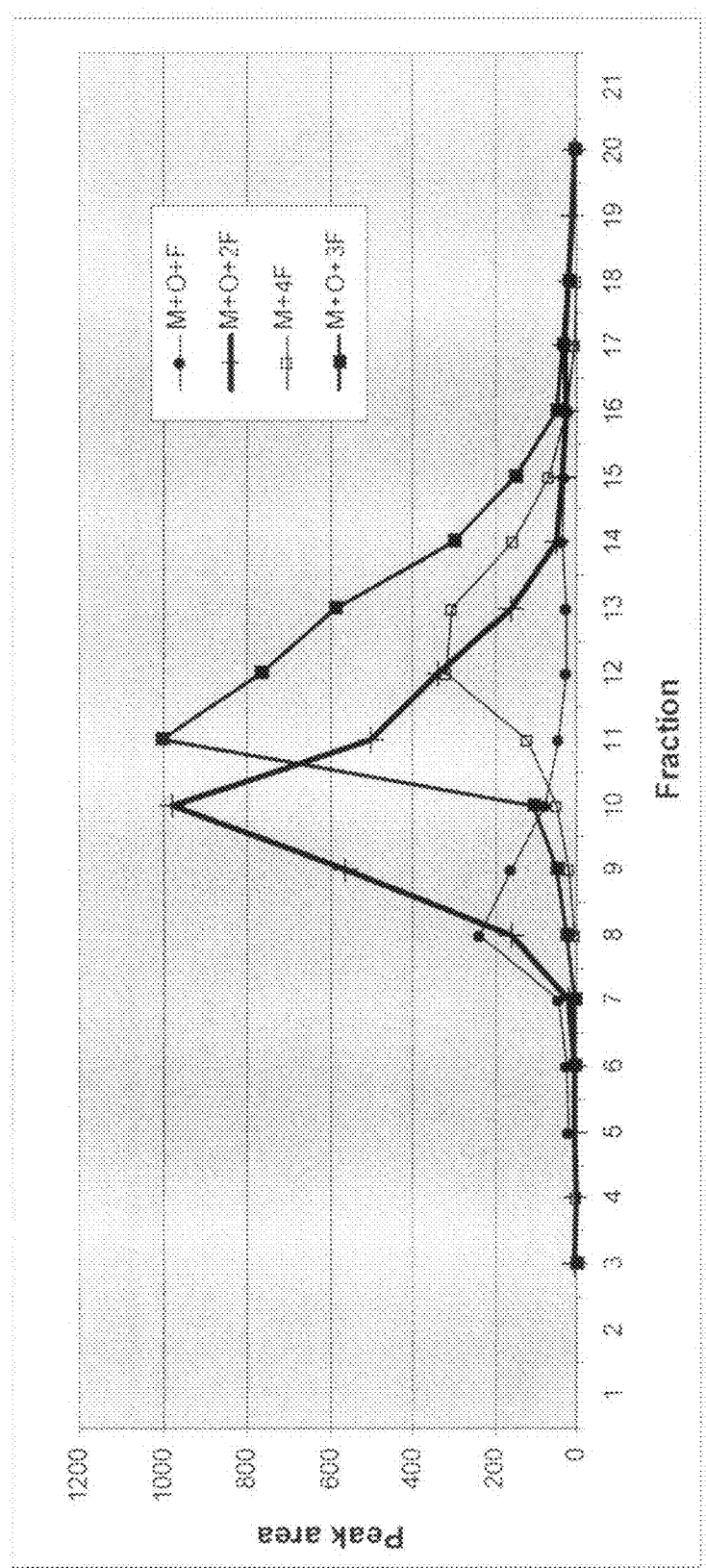

FIG. 9b shows LC-MS analysis of fractions from separation of fraction 19 in FIG. 9a by HPLC.

Figure 10A:
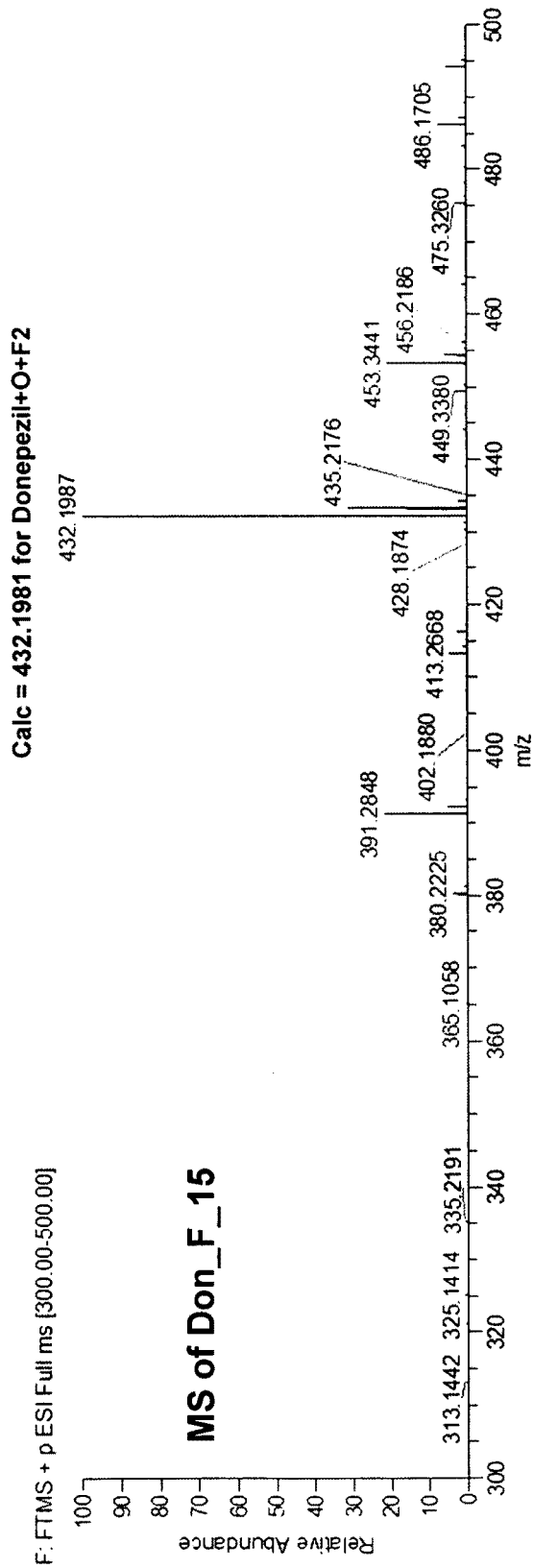
FIGS. 10a, 10b and 10c show LC-MS/MS analysis of purified compound Don_F_15 corresponding to M+O+2F from donepezil fluorination mixture library 1.
Figure 10B:
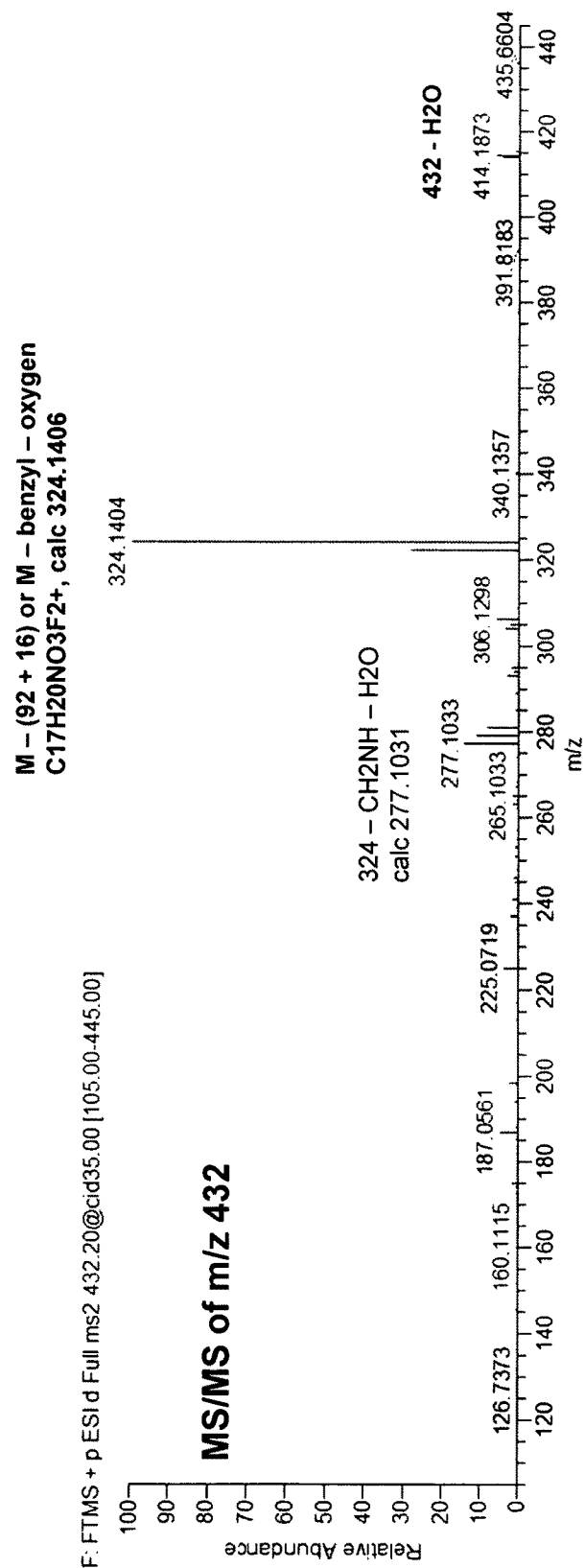
Figure 10C:
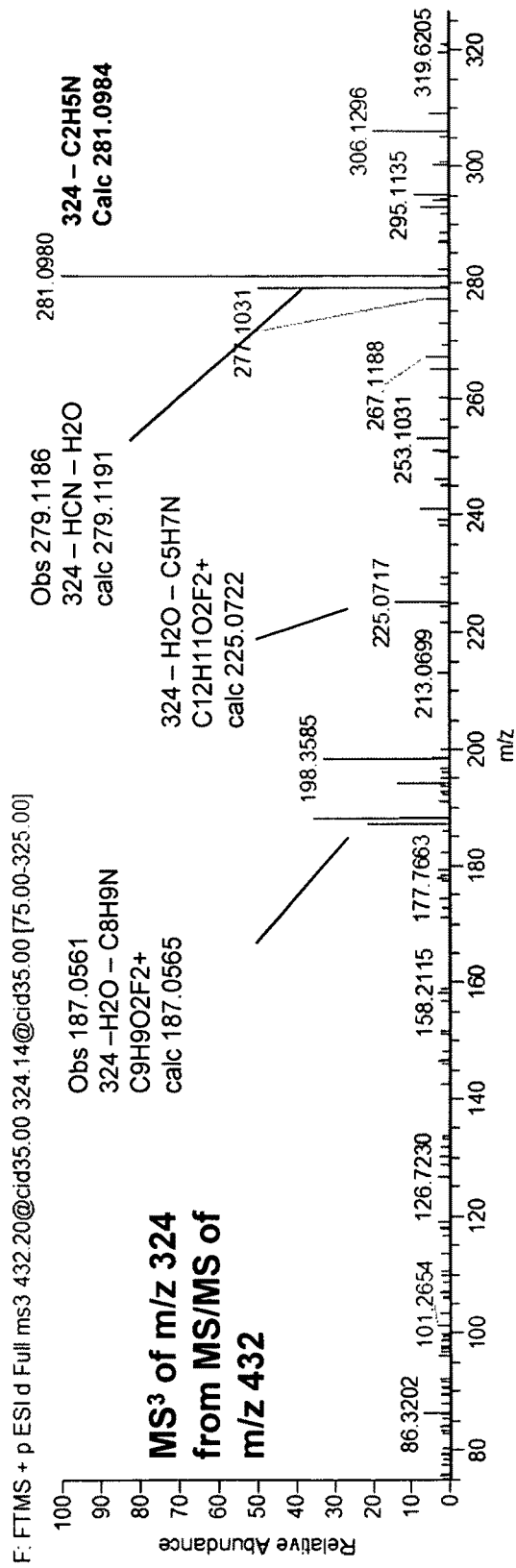

FIG. 10 shows LC-MS/MS and MS3 analysis of purified compound Don_F_15 from donepezil fluorination mixture library 1.

Figure 11:
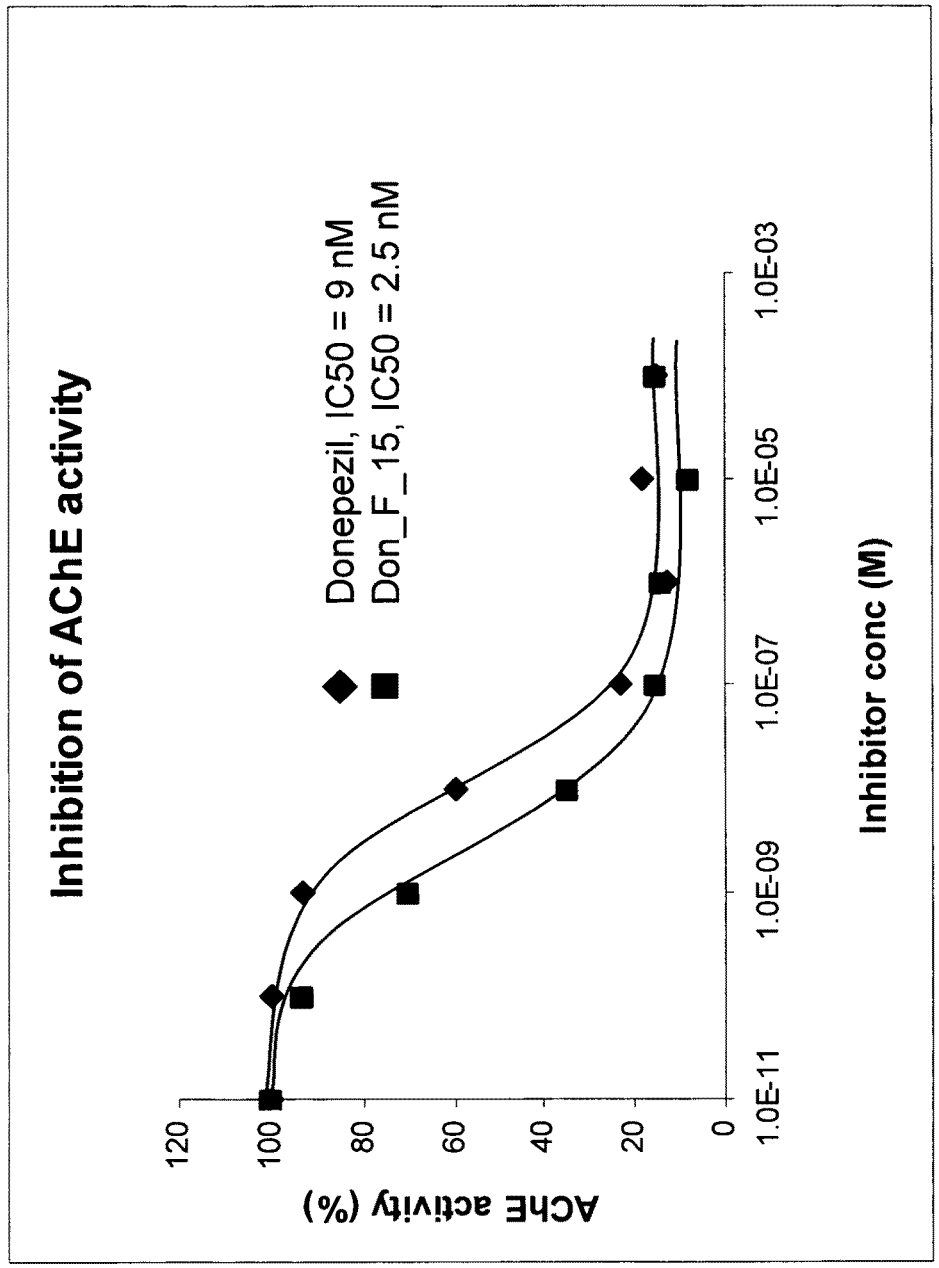
FIG. 11 shows results of AChE enzymatic activity assay of donepezil and purified compound Don_F_15 from donepezil fluorination mixture library 1.

FIG. 11 shows results of AChE enzymatic activity assay of donepezil and purified compound Don_F_15 from donepezil fluorination mixture library 1.

Figure 12A:
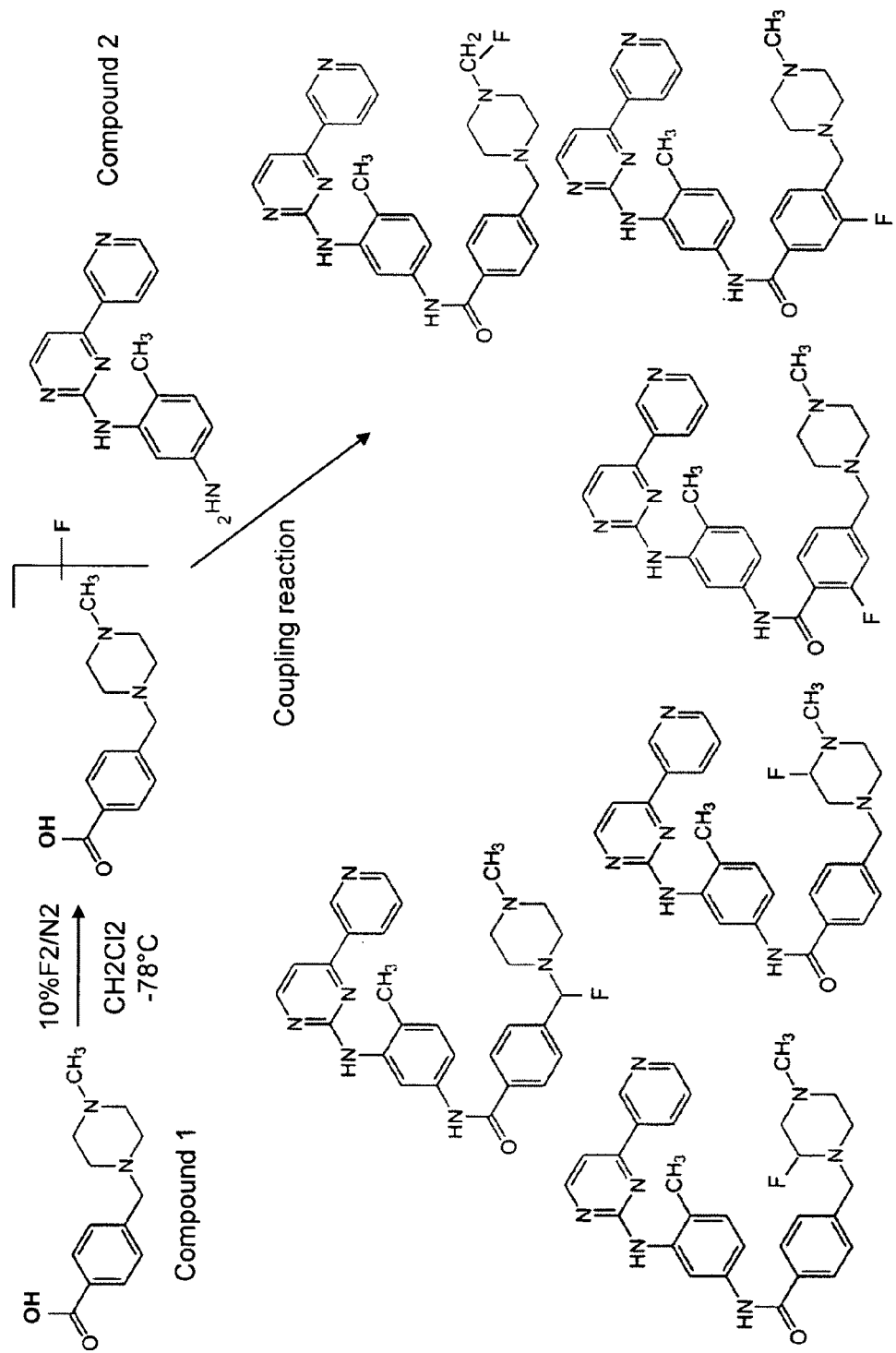
FIGS. 12a and 12b show non-selective modification of gleevec by fluorination reaction of substructures of gleevec and then linking the substructures together.
Figure 12B:
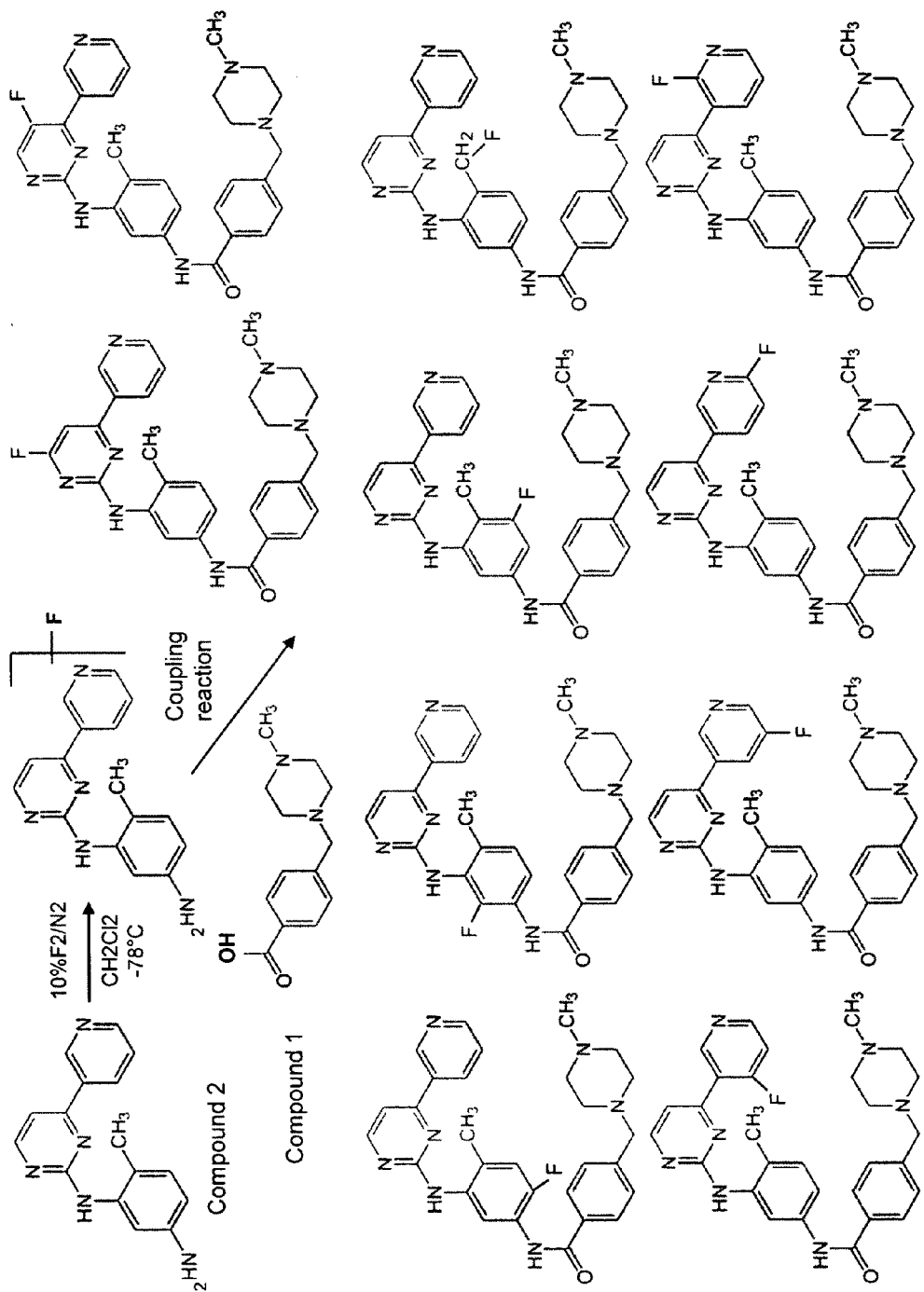

FIGS. 12a and 12b show non-selective modification of gleevec by fluorination reaction of substructures of gleevec and then linking the substructures together. Fluorination of a substructure of gleevec generates a mixture of non-selective C—H bond modification products containing one fluorine atom in each product. Linking of the mixture with a complementary substructure of gleevec produces modified gleevec with one fluorine atom in each product.

The application provides new methods for generating mixture compound libraries from a drug lead by non-selective modification and testing of the mixture compound library for discovery of compounds with improved drug properties. The method preferably includes the following steps in the order given:

Step 1:

Generating of the mixture compound library from a drug lead. This may begin with a non-selective reaction of the drug lead. The products may be a mixture where different structural positions of the drug lead are modified into different products (FIG. 3). Alternatively, one can make non-selective modifications of a substructure compound of a drug lead to produce a mixture where different positions of the drug lead substructure are modified in different products. Then the modified drug lead substructure is linked to a complementary substructure, by a suitable organic reaction, to form the whole of the drug lead structure with non-selective modifications (FIG. 4). Known reactions that will produce non-selective chemical modifications include, but not limited to: reaction with fluorine gas and reaction with hydroxyl radical. Hydroxyl radicals may be generated by high energy radiation (von Sonntag, C. The Chemical Basis of Radiation Biology. Taylor & Francis, London. 1987), by photochemistry (Sharp, J. S.; et al. "Analysis of protein solvent accessible surfaces by photochemical oxidation and mass spectrometry," Anal. Chem. 2004, 76, 672-683), or by processes such as Fenton chemistry (Walling, C., Fenton's reagent revisited. Acc. Chem. Res., 1975, 8 (5), 125-131; Halliwell, B. and Gutteridge, J. M. C. Biologically relevant metal ion-dependent hydroxyl radical generation. An update. FEBS Lett., 1992, 307, 108-112). Oxidation reactions with cytochrom P450 enzymes may also lead to non-selective modification of a drug lead compound, especially if a mixture of different P450 enzymes is used. (Rentmeister, A., et al. Chemo-enzymatic fluorination of unactivated organic compounds, Nature Chemical Biology, 2009, 5 (1), 26-28).

Optionally, the product mixture formed by non-selective reaction of the drug lead is treated with a generic protein such as bovine serum albumin to remove reactive components that may form a covalent bond with a protein; the remaining compound mixture may be recovered by organic solvent extraction or other extraction methods. The non-selective modification product mixture is separated using techniques including HPLC, TLC, GC, et al. into fractions. The mixture compound library is generated by taking one fraction, or several fractions, from this separation and optionally mixing with compounds or mixtures from other sources. A helpful guide for taking the appropriate fractions and mixing with other appropriate fractions of compounds or mixtures of other sources is to generate mixture compound library without any component being predominate in concentration. An important consideration is the removal of a large portion of the unreacted drug lead compound itself since it is often desirable to not let the non-selective reaction to go too far to prevent formation of products where there are too many structural positions of the drug lead being modified in the same product. In that case, where the non-selective reaction is carried out to a very limited degree, the amount of unreacted drug lead compound itself will be dominate in the reaction product mixture. Separation and combining appropriate fractions of the separation can produce a mixture compound library where the excess amount of unreacted drug lead is reduced to the level comparable to that of the products.

Step 2:

Test the products of non-selective modification of the drug lead to discover compounds with improved drug properties relative to the original drug lead compound. Drug properties that may be tested include, but not limited to, the affinity or the activity toward the biological target of the drug lead, human microsomal stability, PAMPA permeability, plasma protein binding, blood brain barrier (BBB) penetration, or the solubility in a drug formulation. For affinity studies one may use affinity separation techniques including: ultrafiltration, size-exclusion chromatography, dialysis and/or affinity chromatography. (Wanner, K. et al., Mass Spectrometry in Medicinal Chemistry: Applications in Drug Discovery, Volume 36, Wiley 2007; Comess, K. M. and Schurdak, M. E., Affinity-based screening techniques for enhancing lead discovery, Current Opinion in Drug Discovery & Development 2004, 7 (4), 411-416)

These techniques, combined with detection methods such as LC-MS or NMR, may be used to determine the relative affinity of mixture components. For activity measurements of a mixture, one may use LC-MS in combination with an on-line bioreactor. (van Liempd, S. M., et al. On-line Formation, Separation, and Estrogen Receptor Affinity Screening of Cytochrome P450-Derived Metabolites of Selective Estrogen Receptor Modulators, Drug Metabolism and Disposition, 2006, 34 (9), 1640-1649; de Jong, C. F., et al. High-performance liquid chromatography-mass spectrometry-based acetylcholinesterase assay for the screening of inhibitors in natural extracts, Journal of Chromatography A, 2006, 1112, 303-

310) For human liver microsomal stability experiment, one may incubate the mixture compound library with human liver microsome preparation and measure concentration of the mixture components with LC-MS or NMR before and after incubation. For PAMPA permeability, which is an indication of the drug's ability to be absorbed by the intestinal system when taken orally, one may use specialized PAMPA plate for compound permeability and use LC-MS to measure compound concentration in two different sides of the PAMPA membrane (apical and basal) to calculate the permeability. For plasma protein binding, dialysis plates may be used to measure free and bound portion of mixture components with LC-MS measurement.

Step 3:

Purify the components that show improved drug properties relative to the drug lead. Drug properties may include, but not limited to: affinity, activity, human microsomal stability, membrane permeability, plasma protein binding, blood-brain-barrier (BBB) penetration, and solubility in a drug formulation. Only the best components may be considered to purify if there are too many components showing improved properties. Preparative liquid chromatography (PrepLC) may be used to purify selected components of the mixture. Mass spectrometry detection and triggering for compound collection may be used to assist the purification of selected components from the mixture. (Blom K. F., et al. Preparative LC-MS purification: improved compound-specific method optimization, J Comb Chem. 2004, 6 (6), 874-83)

The goal of Step 3 is to obtain enough quantity and purity of each compound of interest for full structure determination by NMR. With modern NMR instrumentation, micro gram quantity is adequate for structure determination of an organic compound by those skilled in the art of compound structure determination. (Holzgrabe, U. et al., NMR spectroscopy in drug development and analysis, Wiley-VCH, 1999, Weinheim) It is also possible to determine the structure of the compound from a mixture using LC-MS/MS without purifying the components. (Lee, M. S. Integrated Strategies for Drug Discovery Using Mass Spectrometry, Wiley-Interscience, 2005). After the structure determination of the interesting components of the mixture compound library, the pure form of desired mixture components may be obtained with sufficient amount for in vitro tests to confirm their improved drug properties relative to the starting drug lead. One may obtain sufficient amount of a mixture compound library component by separation and purification of the mixture compound library (scaling up the amount of mixture compound library if necessary) or by organic synthesis of the compound when the structure of the compound is fully determined.

Step 4:

After separation and purification or organic synthesis to obtain sufficient amount, the desired components of the mixture compound library from the drug lead are tested individually for confirmation of improved drug properties relative to the original drug lead. The tests may be similar to Step 2, except that individual components may be tested in Step 4 while mixture compound libraries are tested in Step 2. The confirmation experiments may complete the process of improving the properties of the original drug lead by the novel method invented in this patent.

DETAILED DESCRIPTION OF PREFERRED EMBODIMENTS

In one embodiment of the present method (whole structure modification), a drug lead molecule structure may be modified directly by a non-selective reaction (FIG. 3). This embodiment is suitable for those drug lead structures which are stable under the reaction conditions chosen for the non-selective modification of the drug lead.

In another embodiment of the present method (substructure modification), one or more substructure(s) of a drug lead may be modified, separately, by non-selective reactions. The mixture products of each of the substructure modifications may then be jointed together through appropriate coupling reactions, to form the whole of the modified drug lead structure (FIG. 4). The degree of modification will depend on the degree of structural modification of each of the substructures.

In another embodiment of the present method (combination of selective and non-selective modifications), the mixture compound library may be generated by a combination of the non-selective modification methods described in this method and the traditional methods of modification using selective organic reactions.

In some embodiments (combination of drug leads), the mixture compound library may include modifications for more than one drug lead. Thus, for example, several analog compounds of a drug lead can be put together and this mixture can undergo a non-selective chemical reaction to form a new mixture of compounds for the generation of mixture compound library.

In some embodiments (mixture libraries), the method of generating the mixture compound library can include, but not limited to: directly using the non-selective modification reaction product mixture of the drug lead, or separating the product mixture into fractions and taking one fraction, or mixing selected fractions together, or mixing one or more fractions with compounds or mixtures of other origins.

In some embodiments (treated libraries), the mixture compound library is treated with a generic protein (such as bovine serum albumin) to remove covalent binders of protein from the mixture compound library and recover the remaining compounds by organic solvent extraction or other extraction methods.

In some embodiments, the modified drug lead compound library may be formed by non-selective reactions include, but not limited to: fluorination, Fenton reaction, photochemical reaction, radiation reaction, electrochemical reaction, oxidation reaction, free radical reaction, microwave assisted reaction.

In some embodiments, the drug properties may include, but are not limited to: affinity toward a biological target, functional activity in a biological assay, metabolic stability, PAMPA permeability, plasma protein binding, blood-brain barrier (BBB), solubility in a drug formulation.

In an embodiment of the present method (structure ID first), the structure of a component of the mixture compound library showing improved drug properties may be determined by LC-MS/MS and/or LC-NMR. This compound may then be synthesized by standard organic synthesis technologies by those skilled in the art of organic synthesis and the improved drug properties can be confirmed by appropriate drug property tests of this synthesized compound.

In another embodiment of the present method (separation first), sufficient amount of a component of the mixture compound library showing improved drug properties may be separated and purified by HPLC or LC-MS. This purified compound may then be evaluated by appropriate drug property tests to confirm the improved drug properties. Upon confirmation of improved drug properties, this purified compound may then be structure determined by NMR and/or MS/MS and be synthesized by standard organic synthesis technologies by those skilled in the art of organic synthesis for further development.

EXAMPLES

The following examples are offered to illustrate, but not to limit the claimed method. One of ordinary skill in the art will recognize a variety of non-critical parameters that may be altered without departing from the scope of the claimed method.

Example 1

Non-selective modification of a drug lead by fluorination. 300 mg donepezil was dissolved in 200 mL CH2Cl2 at −78° C. cooled by dry-ice/acetone bath. A mixture of F2 and N2 gas containing 10% F2/80% N2 was passed through the reaction vessel continuously at a flow rate of 2 L/min. At time points of 15, 30, 45, and 60 min, one quarter of the content of the reaction was taken out and the solvent was removed under vacuum. Dried reaction products were dissolved in 3 mL acetonitrile and the solution was analyzed by LC-MS (Agilent 1200, Agilent Eclips 150×4.6 mm column, gradient elution from 10% acetonitrile/90% 0.1% formic acid in dd-H2O to 90% acetonitrile/10% 0.1% formic acid in dd-H2O, 1 ml/min total flow rate, Waters LCT TOFMS in positive ion mode). LC-MS analysis results of selected products for 30 min time point are shown in FIG. 5.

Example 2

Preparation of mixture compound library for testing of drug properties. Reaction mixture of donepezil fluorination was separated on an Agilent Zorbax C8 250×4.6 mm column, gradient elution from 30% MeOH/70% 0.1% formic acid in dd-H2O to 90% MeOH/10% 0.1% formic acid in dd-H2O, 1 ml/min total flow rate). Each fraction was analyzed by LCT mass spectrometer (FIG. 6). Fractions 7-13 contained mostly the unreacted donepezil and were not included in the formation of library. Fractions 14-16 were mixed to form the mixture compound library (donepezil fluorination mixture library 1) for the subsequent testing of drug properties.

Example 3

Affinity testing of compound mixture library. Donepezil fluorination mixture library 1 was mixed with a buffered solution containing 10 uM AChE enzyme (Sigma catalog No C3389) at pH 7.4 (50 mM Tris HCl). The mixture was filtered through a microcon filter with molecular weight cutoff (MWCO) of 10 kDa. New buffer was added to the top of the filter and the solution was filtered through the microcon filter. This process was repeated three times and a portion of the top layer of each filtration was removed and treated with organic solvent acetonitrile to denature the enzyme and to extract the donepezil fluorination mixture library compounds that bound to the enzyme. Compound concentration in the top layer was measured by LC-MS analysis (Agilent 1200, Agilent Eclips 150×4.6 mm, gradient elution from 10% acetonitrile/90% 0.1% formic acid in dd-H2O to 90% acetonitrile/10% 0.1% formic acid in dd-H2O, 1 ml/min total flow rate, Waters LCT TOFMS in positive ion mode), and the relative affinity determined based on the concentration change after each round of filtering through microcon filter. A sample containing the AChE enzyme but without donepezil fluorination mixture library 1 was treated the same way as the sample with donepezil fluorination mixture library 1 to serve as a compound-negative control. The components with larger decrease in concentration in the sample with donepezil fluorination mixture library 1 after each filtering indicate lower affinity and vice versa. (FIG. 7). The affinity testing results for selected compounds are listed below: compound (m/z, RT), affinity toward AChE relative to donepezil:

M+F(398, 4.04), 1.34; M+F(398, 4.18), 1.84; M+2F(416, 4.14), 1.96;

M+2F(416, 4.27), 2.32; M+3F(434, 4.33), 2.76; M+3F(434, 4.47), 2.75;

M+O(396, 3.96), 0.2; M+O(396, 4.29), 2.33; M+O(396, 4.36), 1.88;

M+O+F(414, 3.92), 0.88; M+O+F(414, 4.14), 1.49; M+O+F(414, 4.2), 0.17;

M+O+F(414, 4.46), 2.13; M+O+2F(432, 3.98), 0.67; M+O+2F(432, 4.25), 1.27;

M+O+2F(432, 4.47), 4.55; M+F2(418, 3.84), 0.55; M+2F2(456, 4.02), 0.39;

M+2F2+F(474, 4.07), 0.29; M+4F(452, 4.51), 3.94; M+4F(452, 4.64), 2.02;

M+4F(452, 4.97), 2.96; M+4F(452, 5.14), 2.88.

Example 4

Liver microsome stability testing of compound mixture library. Donepezil fluorination mixture library 1 was mixed with a buffered solution containing human liver microsome (Invitrogen Cat. No. HMMC-PL, 1 mg/mL), 1 mM NADPH in 50 mM KPO4 pH7.4 for 2 hours at 37° C. and then was treated with 4 volumes of organic solvent acetonitrile to stop the metabolism reaction and to extract the donepezil fluorination mixture library 1 compounds. Control samples were also done where the donepezil library 1 was replaced by pure donepezil and by reference compound terfenedine each at 1 uM. The concentration of compounds before and after the microsome incubation was measured by LC-MS analyses (Agilent 1200, Agilent Eclips 150×4.6 mm, gradient elution from 10% acetonitrile/90% 0.1% formic acid in dd-H2O to 90% acetonitrile/10% 0.1% formic acid in dd-H2O, 1 ml/min total flow rate, Waters LCT TOFMS in positive ion mode), and the relative metabolic stability determined based on the concentration change after incubation. The components with larger decrease in concentration after microsome incubation indicate lower metabolic stability and vice versa. (FIG. 8). The metabolic stability testing results for selected compounds are listed below: compound (m/z, RT), metabolic stability relative to donepezil:

M+F(398, 3.64), 1.35; M+F(398, 3.74), 1.52; M+2F(416, 3.71), 2.17;

M+2F(416, 3.80), 1.33; M+3F(434, 3.86), 1.36; M+3F(434, 3.93), 1.43;

M+O(396, 3.58), 1.35; M+O(396, 3.74), 0.89; M+O(396, 3.85), 0.39;

M+O+F(414, 3.54), 1.66; M+O+F(414, 4.14), 1.08; M+O+F(414, 3.83), 1.54;

M+O+F(414, 4.46), 0.96; M+O+2F(432, 3.59), 1.62; M+O+2F(432, 3.82), 1.4;

M+O+2F(432, 3.90), 1.39; M+O+2F(432, 3.96), 1.36; M+F2(418, 3.50), 1.19;

M+F2+F(436, 3.78), 0.73; M+2F2(456, 3.69), 1.23; M+2F2+F(474, 3.80), 0.97;

M+2F2+F(474, 3.91), 1.19; M+2F2+2F(492, 3.67), 1.15; M+2F2+2F(492, 3.84), 1.45;

M+2F2+2F(492, 3.96), 1.12; M+4F(452, 3.44), 1.49; M+4F(452, 3.96), 1.27;

M+4F(452, 4.04), 1.4; M+4F(452, 4.97), 1.65; M+4F(452, 5.14), 1.82.

Example 5

Enzymatic activity assay. Donepezil fluorination mixture library 1 is separated by an HPLC device (Agilent 1200, Agilent Eclips 150×4.6 mm, gradient elution from 10% MeOH/90% 10 mM NH4OAc (pH 7) to 40% MeOH/60% 10 mM NH4OAc (pH 7), 1 ml/min total flow rate. The eluent of the HPLC is continuously passed through a buffered flow reactor cell containing AChE enzyme with a substrate acetylcholine at pH 7 and analyzed by mass spectrometer (Waters LCT-TOF in positive ion mode). The inhibition effect and the identity of the components are monitored by the intensity change of the substrate acetylcholine, the formation of enzymatic reaction product choline and the corresponding mass of the mixture component eluting out at the time. Relative inhibition of AChE activity of components of the donepezil fluorination mixture library 1 vs. donepezil itself is determined.

Example 6

Purification of compound showing improved drug properties. Compound Don_F_15 having a molecular weight consistent with M+O+2F and Don_F_18 having a molecular weight consistent with M+O+3F were purified first using a preparative HPLC (Shimadzu 10ADVP, Supelco Discovery RP Amide C16, MeOH/0.1% formic acid-ddH2O gradient) and then using another preparative HPLC column (Thermo PFP Gold, 4.6×250 mm, 80% MeOH/0.1FA/20% H2O) with mass spectrometry and UV detection (FIG. 9). LC-MS/MS (Thermo Finnigan LCQ Orbitrap) analysis identified the structure of the compound. (FIG. 10).

The fragment ions observed from LC-MS/MS and MS3 analysis of purified Don_F_15 are listed below:
Assignment Formula m/z (calc) m/z (obs)
M C24H28NO4F2+ 432.1981 432.1987
M-H2O C24H26NO3F2+ 414.1875 414.1873
M-Bz-O+2 C17H20NO3F2+ 324.1406 324.1404
M-Bz-O C17H18NO3F2+ 322.1249 322.1248
324-H2O C17H18NO2F2+ 306.1300 306.1296
324-CH3N C16H17O3F2+ 295.1140 295.1138
324-CH5N C16H15O3F2+ 293.0984 293.0977
324-C2H5N C15H15O3F2+ 281.0984 281.0980, 281.0981
324-H2O—HCN C16H17O2F2+ 279.1191 279.1186, 279.1189
324-H2O—CH3N C16H15O2F2+ 277.1035 277.1031, 277.1033
324-H2O—C3H3N C14H15O2F2+ 253.1035 253.1031
324-C5H9N C12H11O3F2+ 241.0671 241.0668
324-H2O—C5H7N C12H11O2F2+ 225.0722 225.0717, 225.0719
324-H2O—C6H7N C11H11O2F2+ 213.0722 213.0718, 213.0699
324-H2O—C8H9N C9H9O2F2+ 187.0565 187.0561
C6H10N+ 96.0808 96.0802
M=Donepezil+O+2F Example 7

Confirmation of compound showing improved drug properties. The purified compounds Don_F_15 and Don_F_18 were tested individually for affinity, metabolic stability and activity. The procedures were the same as example 3-5 except a single purified compound is used in example 7 while a mixture of compounds is used in examples 3-5. The results confirm that Don_F_15 and Don_F_18, after purification into single pure compounds, show higher affinity toward AChE enzyme, greater metabolic stability in human microsomal incubation, and higher activity toward AChE enzyme compared to donepezil itself. Additionally, AChE enzymatic activity assay was conducted using Ellman method (Ellman, G. L., et al, Biochem. Pharmacol., 7, 88-95, 1961, colorimetric method; color indicator, DTNB, measuring absorption at 405 nm; AChE enzyme, 10 mU/mL; substrate Acetylthiocholine Iodide, 75 mM; 100 mM phosphate buffer, pH 7.4) FIG. 11 shows results of AChE enzymatic activity assay of donepezil and purified compound Don_F_15 from donepezil fluorination mixture library 1 using the Ellman colormetric method.

Example 8

Substructure embodiment. Compound 1 (substructure-1 of gleevec) is dissolved in $CH_2Cl_2$ at −78° C. cooled by dry-ice/acetone. A mixture of F2 and N2 gas containing 10% F2 is passed through the reaction vessel continuously. At time points of 15, 30, 45, and 60 min, one quarter of the content of the reaction is taken out and the solvent removed under vacuum. Dried reaction products are dissolved in acetonitrile and the content analyzed by LC-MS (Agilent 1200, Agilent Eclips 150×4.6 mm, gradient elution from 10% acetonitrile/90% 0.1% formic acid in dd-H2O to 90% acetonitrile/10% 0.1% formic acid in dd-H2O, 1 ml/min total flow rate, Waters LCT TOFMS in positive ion mode). The expected products is a mixture and are shown in FIG. 12a, step 1. This product mixture is then reacted with compound 2 (substructure-2 of gleevec) under the catalysis of DCC to produce a mixture of modified gleevec as expected products showing in the second step of FIG. 12a.

Example 9

Compound 2 (substructure-2 of gleevec) is dissolved in CH2Cl2 at −78° C. cooled by dry-ice/acetone. A mixture of F2 and N2 gas containing 10% F2 is passed through the reaction vessel continuously. At time points of 15, 30, 45, and 60 min, one quarter of the content of the reaction is taken out and the solvent removed under vacuum. Dried reaction products are dissolved in acetonitrile and the content analyzed by LC-MS (Agilent 1200, Agilent Eclips 150×4.6 mm, gradient elution from 10% acetonitrile/90% 0.1% formic acid in dd-H2O to 90% acetonitrile/10% 0.1% formic acid in dd-H2O, 1 ml/min total flow rate, Waters LCT TOFMS in positive ion mode). The expected products is a mixture and are shown in FIG. 6b, step 1. This product mixture is then reacted with compound 1 catalyzed by DCC to produce a mixture of modified gleevec as expected products showing in the second step of FIG. 12b.

Example 10

The product mixture from Example 8 and 9 is mixed with a buffered solution containing bcr-abl kinase enzyme at pH 7. The mixture is filtered through a microcon filter with molecular weight cutoff (MWCO) of 10 kDa. New buffer is added to the top of the filter and the solution is filtered through the microcon filter. This process is repeated three times and a portion of the top layer of each filtration is removed and treated with organic solvent acetonitrile to denature the enzyme and to extract the ibuprofen and its fluorine modification products. Compound concentration in the top layer is measured by LC-MS analysis and the relative affinity determined based on the concentration change after each round of filtering through microcon filter. The components with larger decrease in concentration after each filtering indicate lower affinity and vice versa.

Example 11

The product mixture from Example 8 and 9 is separated by an HPLC device. The eluent of the HPLC is continuously passed through a buffered flow reactor cell containing bcr-abl kinase enzyme with a substrate peptide at pH 7 and analyzed by LC-MS. The inhibition effect and the identity of the components are monitored by the intensity change of the substrate peptide, the formation of enzymatic reaction product phosphopeptide and the corresponding mass of the mixture component eluting out at the time.

Example 12

The product mixture from Example 9 is mixed with a buffered solution containing human liver microsome preparation and cofactors for metabolism. The mixture is incubated for 30 min at 37° C. and then is treated with organic solvent acetonitrile to stop the metabolism reaction and to extract the ibuprofen and its fluorine modification products. The concentration of compounds before and after the microsome incubation is measured by LC-MS, 1H-NMR and 19F-NMR analyses and the relative metabolic stability determined based on the concentration change after incubation. The components with larger decrease in concentration after microsome incubation indicate lower metabolic stability and vice versa.

Example 13

The data from experiments 10-12 are examined and the components with improved properties judging by the affinity/activity toward bcr-abl kinase enzymes or metabolic stability in human microsome incubation are identified. These components are purified using a preparative HPLC with mass spectrometry and UV detection to obtain 0.5-1 mg for each compound of interest. NMR and/or MS/MS analyses confirm the structure of the purified compounds.

Example 14

The purified compounds are tested individually for affinity and activity toward bcr-abl kinase enzymes and for metabolic stability with human liver microsome preparation. The procedures are the same as examples 10-12 except a single purified compound is used in example 15 while a mixture of compounds is used in examples 10-12. The results confirm that certain modified drug lead compounds, after purification into single pure compounds, show higher affinity and activity toward bcr-abl kinase enzymes or have better metabolic stability than the original drug lead compound.

Example 15

Donepezil fluorination mixture library 1 is treated with 1 mg/mL concentration bovine serum albumin for 30 min in 10 mM NH4OAc (pH 7) to remove compounds that can covalently modify a protein, and then extracted with an organic solvent (acetonitrile) before using the mixture library for testing of drug properties.

Example 16

Exemplary MS or LC-MS Protocol. Samples are analyzed by mass spectrometry alone or by liquid chromatography coupled to mass spectrometry, or other analytical techniques such as NMR, for the quantity and identity of components of the mixture compound libraries described in this method.

Mass spectrometry: Analysis may be performed on, e.g., time-of-flight mass spectrometers LCT (Waters Corporation, Milford, Mass., USA) using an Z-spray (electrospray) ionization source. The electrospray voltage is generally maintained in the range of about 3.5-4.0 kV. Ion optics settings are optimized on the day of the analysis to provide the maximum efficiency of ion to the detector. The effective mass range is generally from m/z 100 to m/z 1000 at a rate of about 1 s/scan.

Liquid chromatography: For example, samples can be introduced through an Agilent 1200 (Agilent Technologies, Santa Clara, Calif., USA) chromatography operating in the gradient mode at a flow rate of 1 ml/min. An Eclips C18 base-deactivated column (4.6 mm×15 cm) from Agilent is used for sample separation. The mobile phase gradient is H2O+ACN 90/10 (v/v) containing 0.1% formic acid to a H2O+ACN 10/90 (v/v) containing 0.1% formic acid in 10 minutes. Samples are introduced through an autosampler as part of the Agilent 1200. The sample injection volumes are generally 1-20 µL.

It is apparent from the above results and discussion that a novel method of generating mixture compound library and screening the library for the purpose of discovering compounds with improved drug properties are provided by the subject method. These methods can find wide application in drug discovery and development. Also provided are novel methods of non-selective modification of a drug lead structure. Accordingly, the subject method provides for a significant contribution to the field.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present method is not entitled to antedate such publication by virtue of prior methods.

Although embodiments of the method are shown and described therein, it should be understood that various changes and modifications to the presently preferred embodiments will be apparent to those skilled in the art. Such changes and modifications may be made without departing from the spirit and scope of the method and without diminishing its attendant advantages. It is, therefore, intended that such changes and modifications be covered by the appended claims.

US PATENT REFERENCES

Nikolai F. Sepetov, et al. U.S. Pat. No. 6,799,120—Nonredundant split/pool synthesis of combinatorial libraries, US Patent Issued on Sep. 28, 2004.

Other References

Nogrady, T. and Weaver, D. F., Medicinal chemistry: a molecular and biochemical approach, Oxford University Press, 2005

Thomas, G., Fundamentals of medicinal chemistry, Wiley, New York, 2003.

Corey, E. J. and Cheng, X.-M., The Logic of Chemical Synthesis, Wiley, New York, 1989.

Lam, K. S., et al. "The 'one-bead-one-compound' combinatorial library method," Chem. Rev. 1997, 97, 411-448.

Furka, A. and Bennett, W. D. "Combinatorial libraries by portioning and mixing," Comb. Chem. High Throughput Screening 1999, 2, 105-122.

Gardiner, I. V., Fluorine Chemistry Research Advances, 2007, Nova Science Publishers, Inc. 2007.

Pearson, B., Specialty Chemicals, Spring Innovations Ltd, 1991.

Walling, C., Fenton's reagent revisited. Acc. Chem. Res., 1975, 8 (5), 125-131.

Halliwell, B. and Gutteridge, J. M. C. Biologically relevant metal ion-dependent hydroxyl radical generation. An update. FEBS Lett., 1992, 307, 108-112.

von Sontag, C. The Chemical Basis of Radiation Biology. Taylor & Francis, London. 1987.

Sharp, J. S.; et al. "Analysis of protein solvent accessible surfaces by photochemical oxidation and mass spectrometry," Anal. Chem. 2004, 76, 672-683.

Rentmeister, A., et al. Chemo-enzymatic fluorination of unactivated organic compounds, Nature Chemical Biology, 2009, 5 (1), 26-28.

Wanner, K. et al., Mass Spectrometry in Medicinal Chemistry: Applications in Drug Discovery, Volume 36, Wiley 2007.

Comess, K. M. and Schurdak, M. E., Affinity-based screening techniques for enhancing lead discovery, Current Opinion in Drug Discovery & Development 2004, 7 (4), 411-416.

Klages, J. et al. NMR-based screening: a powerful tool in fragment-based drug discovery, Analyst, 2007, 132, 692-705.

Lepre, C. A., et al. Theory and applications of NMR-based screening in pharmaceutical research. Chemical Reviews, 2004, 104 (8), 3641-3675.

Halladay, J. S. et al. Metabolic Stability Screen for Drug Discovery Using Cassette Analysis and Column Switching, Drug Metabolism Letters, 2007, 1, 67-72.

Blom K. F., et al. Preparative LC-MS purification: improved compound-specific method optimization, J Comb Chem. 2004, 6 (6), 874-83.

van Liempd, S. M., et al. On-line Formation, Separation, and Estrogen Receptor Affinity Screening of Cytochrome P450-Derived Metabolites of Selective Estrogen Receptor Modulators, Drug Metabolism and Disposition, 2006, 34 (9), 1640-1649.

de Jong, C. F., et al. High-performance liquid chromatography-mass spectrometry-based acetylcholinesterase assay for the screening of inhibitors in natural extracts, Journal of Chromatography A, 2006, 1112, 303-310.

Holzgrabe, U. et al., NMR spectroscopy in drug development and analysis, Wiley-VCH, 1999, Weinheim.

Lee, M. S. Integrated Strategies for Drug Discovery Using Mass Spectrometry, Wiley-Interscience, 2005.

What is claimed is:

1. A method of generating mixture compound libraries and screening the libraries for the discovery of compounds with improved drug properties, comprising the steps of:
    (a) providing a drug lead compound showing biological activity;
    (b) generating a mixture compound library from the drug lead compound by using a non-selective fluorination reaction with fluorine gas;
    (c) testing the mixture compound library of a plurality of fluorinated compounds to detect compounds with improved drug properties including binding affinity toward a biological target;
    (d) testing the mixture compound library to detect compounds with improved metabolic stability;
    (e) identifying the structure of compounds showing improved drug properties;
    (f) isolating or synthesizing the identified compounds with improved drug properties; and
    (g) testing individual isolated or synthesized compounds to confirm the improved drug properties.

2. The method of claim 1, wherein the method of generating the mixture compound library is by using a non-selective reaction product mixture from a drug lead or by mixing together two or more non-selective reaction product mixtures from a drug lead.

3. The method of claim 1, wherein the method of generating the mixture compound library is by mixing the non-selective reaction products from a drug lead with individual compounds or compound mixtures of other origins.

4. The method of claim 1, wherein the method of generating the mixture compound library is by partially separating a mixture compound library and taking one fraction of the separation or mixing two or more fractions from the separation or mixing with compounds or libraries of other sources.

5. The method of claim 1, wherein the method of generating the mixture compound library is by treating a mixture compound library with a bovine serum albumin to remove compounds that covalently modify a protein, and then extracting with an organic solvent to recover the remaining compounds.

6. The method of claim 1, wherein the non-selective modification of a drug lead is accomplished by using the drug lead directly or by first non-selective modification of a substructure or substructures of the drug lead and then chemically linking of the substructures together to form the whole of the modified drug lead.

7. The method of claim 1, wherein the testing of the mixture compound library tests for the binding affinity of the drug lead toward a biological target.

8. The method of claim 7, wherein the method of testing the mixture compound library uses ultrafiltration to determine the affinity of the drug lead toward a biological target of the mixture compound library.

9. The method of claim 7, wherein the method of testing the mixture compound library for the affinity of the drug lead toward a biological target of the mixture compound library uses: size-exclusion chromatography, affinity chromatography, dialysis, ultracentrifugation, or electrophoresis.

10. The method of claim 1, wherein the testing of the mixture compound library tests for metabolic stability of the drug lead using extracted human or animal tissues, including: liver, microsome from liver homogenate, hepatocytes, muscle, lung, kidney, or brain is the method of testing the mixture compound library.

11. The method of claim 1, wherein the testing of the mixture compound library tests for compound permeability through a real or artificial cell membrane, a tissue, an organ is the method of testing the mixture compound library.

12. The method of claim 1, wherein the testing of the mixture compound library tests: the plasma protein binding of the drug lead, the blood-brain barrier (BBB) penetration of the drug lead, or solubility in a drug formulation of the drug lead.

13. The method of claim 1, wherein the method for testing the mixture compound library is liquid chromatography mass spectrometry (LC-MS) testing.

14. The method of claim 1, wherein the methods for testing the mixture compound library include, but not limited to: nuclear magnetic resonance (NMR) testing, gas chromatography mass spectrometry (GC-MS) testing, or capillary electrophoresis (CE) testing.

15. The method of claim 1, wherein the method of isolating the new compounds from the mixture compound library is by liquid chromatography (LC).

16. The method of claim 1, wherein the method of isolating the mixture compound library include, but not limited to, utilizing: gas chromatography (GC), thin layer chromatography (TLC), or counter current chromatography (CCC).

17. The method of claim 1, wherein the method of identifying the structure of the new compound showing improved drug properties is tandem mass spectrometry (MS/MS).

18. The method of claim 1, wherein the method of identifying the structure of the new compound showing improved drug properties is LC-MS/MS.

19. The method of claim 1, wherein the method of identifying the structure of the new compound showing improved drug properties is NMR.

20. The method of claim 1, step b, wherein fluorination reaction uses a mixture of fluorine gas and an inert carrier gas.

21. The method of claim 20, wherein the inert carrier gas is nitrogen or argon.

22. The method of claim 1, step c, wherein the method of testing binding affinity uses ultrafiltration and mass spectrometry.

23. The method of claim 1, step c, wherein the method of testing binding affinity uses size-exclusion chromatography and mass spectrometry.

24. The method of claim 1, step d, wherein the method of testing metabolic stability uses human and animal liver microsome homogenate.

25. The method of claim 1, step e, wherein the method of identifying compound structure utilizes liquid chromatography mass spectrometry (LC-MS).

26. The method of claim 1, step e, wherein the method of identifying compound structure utilizes nuclear magnetic resonance (NMR).

27. The method of claim 1, step e, wherein the method of identifying compound structure utilizes gas chromatography mass spectrometry (GC-MS).

28. The method of claim 1, step f, wherein the method of isolating compounds uses liquid chromatography (LC).

29. The method of claim 1, step f, wherein the method of isolating compounds uses gas chromatography (GC).

* * * * *